(12) United States Patent
Weissleder et al.

(10) Patent No.: US 9,999,689 B2
(45) Date of Patent: Jun. 19, 2018

(54) IMAGING BETA CELL MASS

(71) Applicant: The General Hospital Corporation, Boston, MA (US)

(72) Inventors: Ralph Weissleder, Peabody, MA (US); Thomas Reiner, Weehawken, NJ (US); Edmund J. Keliher, Topsfield, MA (US)

(73) Assignee: The General Hospital Corporation, Boston, MA (US)

( * ) Notice: Subject to any disclaimer, the term of this patent is extended or adjusted under 35 U.S.C. 154(b) by 0 days. days.

(21) Appl. No.: 15/076,466

(22) Filed: Mar. 21, 2016

(65) Prior Publication Data

US 2016/0263250 A1 Sep. 15, 2016

Related U.S. Application Data

(63) Continuation of application No. 14/003,959, filed as application No. PCT/US2011/041986 on Jun. 27, 2011, now Pat. No. 9,289,516.

(60) Provisional application No. 61/450,754, filed on Mar. 9, 2011.

(51) Int. Cl.
| | | |
|---|---|---|
| *A61K 38/00* | (2006.01) | |
| *A61K 49/00* | (2006.01) | |
| *A61K 51/08* | (2006.01) | |

(52) U.S. Cl.
CPC ...... *A61K 49/0056* (2013.01); *A61K 49/0032* (2013.01); *A61K 51/08* (2013.01)

(58) Field of Classification Search
None
See application file for complete search history.

(56) References Cited

U.S. PATENT DOCUMENTS

| | | | |
|---|---|---|---|
| 8,980,220 B2 | 3/2015 | Saji et al. | |
| 2003/0091507 A1 | 5/2003 | Holst et al. | |
| 2005/0249668 A1 | 11/2005 | Weissleder et al. | |
| 2006/0269942 A1 | 11/2006 | Kolb et al. | |
| 2008/0050312 A1* | 2/2008 | Kung | A61K 51/0455 424/1.89 |
| 2008/0181847 A1 | 7/2008 | Robillard et al. | |
| 2009/0180953 A1 | 7/2009 | Gotthardt et al. | |
| 2009/0186819 A1 | 7/2009 | Carrier et al. | |
| 2010/0137558 A1 | 6/2010 | Lee et al. | |
| 2010/0204105 A1* | 8/2010 | Riber | C07K 14/605 514/1.1 |

FOREIGN PATENT DOCUMENTS

WO WO 2007/144200 12/2007

OTHER PUBLICATIONS

Means et al. Chemical Modification of Proteins: History and Applications, Bioconjugate Chem. 1990, 1, 2-12.*
Alencar et al., "Novel multiwavelength microscopic scanner for mouse imaging," Neoplasia, 2005, 7:977-83.
Balcar et al., Reaktivität von stickstoff-heterocyclen Genenüber cyclooctin als dienophile, Tetrahedron Letter, 1983, 24: 1481-1484 (with English abstract).
Bao et al., "Second harmonic generation imaging via nonlinear endomicroscopy," Optics Express, Jan. 2010, 18(2): 1255-1260.
Beatty, "Chemical strategies for tagging and imaging the proteome," Mol Biosyst. Aug. 2011;7(8):2360-7 (Abstract Only).
Blackman et al., "Tetrazine ligation: fast bioconjugation based on inverse-electron-demand Diels-Alder reactivity," J Am Chem Soc,, Sep. 2008, 130: 13518-9.
Cao et al., "Fluorescence laparoscopy imaging of pancreatic tumor progression in an orthotopic mouse model," Surgical Endoscopy, Jan. 2011, 25(1): 48-54.
Devaraj et al., "Fast and sensitive pretargeted labeling of cancer cells through a tetrazine/trans-cyclooctene cycloaddition," Angew Chem Int Ed Engl, 2009, 48: 7013-6.
Devaraj et al., "Tetrazine-based cycloadditions: application to pretargeted live cell imaging," Bioconjug Chem,, Dec. 2008, 19: 2297-9.
Devaraj et al., "Bioorthogonal turn-on probes for imaging small molecules inside living cells," Angew Chem Int Ed Engl, Apr. 2010, 49: 2869-72.
Fink et al., "History, goals, and technique of laparoscopic pancreatic necrosectomy," Journal of Gastrointestinal Surgery, Jul. 2011, 15(7): 1092-7.
Friess et al., "The role of diagnostic laparoscopy in pancreatic and periampullary malignancies," Journal of the American College of Surgeons, Jun. 1998, 186(6): 675-682.
Glazer, et al., "Specific chemical modification of proteins," Annu. Rev. Biochem., 1970, 39: 101-30.
Gromada et al., "Stimulation of cloned human glucagon-like peptide 1 receptor expressed in HEK 293 cells induces cAMP-dependent activation of calcium-induced calcium release," FEBS Lett, 1995, 373:182-6.
Hangauer and Bertozzi, "A FRET-based fluorogenic phosphine for live-cell imaging with the Staudinger ligation," Angew Chem Int Ed Engl, 2008, 47: 2394-7.
Harjutsalo et al., "Time trends in the incidence of type 1 diabetes in Finnish children: a cohort study," Lancet, 2008, 371:1777-82.
International Search Report and Written Opinion dated Sep. 3, 2012 in international application No. PCT/ US2011/041986, 13 pages.
Kalvie and White, "Pancreatic Islet Cell Tumors and Hyperplasia: Experience in 14 Hospitals," Ann Surg., Mar. 1972, 175(3): 326-335.
Karvonen et al., "Incidence of Childhood Type 1 Diabetes Worldwide," Diabetes Care, 2000, 23:1516-26.
Keliher et al., "High-yielding, two-step 18F labeling strategy for 18F-PARP1 inhibitors," Chem. Med. Chem., 2011, 6:424-427 (Author Manuscript).
Lee et al., "Peptide-based probes for targeted molecular imaging," Biochemistry 49(7): 1364-1376 (2010).
Lemieux et al., "A fluorogenic dye activated by the staudinger ligation," J Am Chem Soc, Apr. 2003, 125: 4708-9.

(Continued)

*Primary Examiner* — Jeanette Lieb
(74) *Attorney, Agent, or Firm* — Fish & Richardson P.C.

(57) ABSTRACT

The present disclosure provides compositions and methods based on peptide-detectable agent conjugates that are useful for imaging beta cell mass.

14 Claims, 29 Drawing Sheets

(56) References Cited

OTHER PUBLICATIONS

Liew et al., "The pseudokinase tribbles homolog 3 interacts with ATF4 to negatively regulate insulin exocytosis in human and mouse β cells," J Clin Invest, 2010, 12:2876-88.

Montanya et al., "Pancreatic remodeling: beta-cell apoptosis, proliferation and neogenesis, and the measurement of beta-cell mass and of individual beta-cell size," Methods Mol Biol. 2009;560:137-58 (Abstract Only).

Onkamo et al., Worldwide increase in incidence of Type I diabetes—the analysis of the data on published incidence trends, Diabetologia, 1999, 42: 1395-403.

Patterson et al., "Incidence trends for childhood type 1 diabetes in Europe during 1989-2003 and predicted new cases 2005-20: a multicentre prospective registration study," Lancet, 2009, 373:2027-33.

Pipkorn et al., "Inverse-electron-demand Diels-Alder reaction as a highly efficient chemoselective ligation procedure: synthesis and function of a BioShuttle for temozolomide transport into prostate cancer cells," J Pept Sci, Mar. 2009, 15: 235-41.

Prescher et al., "Chemical remodelling of cell surfaces in living animals," Nature, Aug. 2004, 430(7002): 873-877.

Reiner et al., "Near-infrared fluorescent probe for imaging of pancreatic beta cells," Bioconjug Clem. 21(7): 1362-1368 (2010).

Reiner et al., "Synthesis and in vivo imaging of a 18F-labeled PARP1 inhibitor using a chemically orthogonal scavenger-assisted high-performance method," Angew Chem Int Ed Engl. Feb. 18, 2011;50(8):1922-5 (Author Manuscript).

Reiner et al., $^{18}$F-PET imaging of beta cell mass via synthetic GLP1-R analogs, 7 pages, 2011 (unpublished manuscript).

Reiner, et al., "Accurate measurement of pancreatic islet β-cell mass using a second-generation fluorescent exendin-4 analog," PNAS, 2011, 108(31):12815, 6 pages.

Rostovtsev et al., "A stepwise huisgen cycloaddition process: copper(I)-catalyzed regioselective "ligation" of azides and terminal alkynes," Angew Chem Int Ed Engl, 2002, 41:2596-9.

Sauer et al., "Reactions of 1,2,4,5-tetrazines with olefins. The structure of dihydropyridazines," Chem Ber, 1965, 998: 1435-1445 (with English translation).

Sheth et al., "Improved Detection of Ovarian Cancer Metastases by Intraoperative Quantitative Fluorescence Protease Imaging Pre-Clinical Model," Gynecol Oncol., 2009, 112:616-22.

Shore et al., "Review article: chemotherapy for pancreatic cancer," Alimentary Pharmacology & Therapeutics, Dec. 2003, 18(11): 1049-1069.

Sivakumar et al., "A fluorogenic 1,3-dipolar cycloaddition reaction of 3-azidocoumarins and acetylenes," Org Lett, Nov. 2004, 6: 4603-6.

Sletten and Bertozzi, "Bioorthogonal chemistry: fishing for selectivity in a sea of functionality," Angew. Chem. Int. Ed., 2009, 48:6974-6998 (Author Manuscript).

Thalhammer et al., "Reaktivität einfacher offenkettiger und cyclischer dienophile bei Diels-Alder-reaktionen mit inversem elektronenbedarf," Tet Lett, 1990 47:6851-6854 (with English summary).

Upadhyay et al., "Quantitative real-time catheter-based fluorescence molecular imaging in mice," Radiology, 2007, 245:523-31.

Widmann et al., "Agonist-induced internalization and recycling of the glucagon-like peptide-1 receptor in transfected fibroblasts and in insulinomas," Biochem J., 1995, 310:203-14.

Wu et al., "Scanning all-fiber-optic endomicroscopy system for 3D nonlinear optical imaging of biological tissues," Optics Express, May 2009, 17(10): 7907-7915.

Zhou and Fahrni, "A fluorogenic probe for the copper(I)-catalyzed azide-alkyne ligation reaction: modulation of the fluorescence emission via 3(n,pi)-1(pi,pi) inversion," J Am Chem Soc,, Jul. 2004, 126: 8862-3.

* cited by examiner

FIG. 1A

| Name | Abbreviation | Amino Acid sequence | Length (aa) | NIRF mod | MW (kDa) |
|---|---|---|---|---|---|
| Glucagon-like peptide-1 | GLP1 | HAEGTFTSDVSSYLEGQAAKEFIAWLVKGR | 30 | none | 3299 |
| Exendin-4 | E4 | HGEGTFTSDLSKQMEEEAVRLFIEWLKNGGPSSGAPPPS | 39 | none | 4188 |
| Exendin-4(40-Pra) | E4$_{40}$-Pra | HGEGTFTSDLSKQMEEEAVRLFIEWLKNGGPSSGAPPPSX | 40 | none | 4282 |
| Exendin-4(40-Fl) | E4$_{40}$-Fl | HGEGTFTSDLSKQMEEEAVRLFIEWLKNGGPSSGAPPPSX(NIRF) | 40 | Pra40 | 5623 |
| Exendin-4(K12Fl) | E4$_{K12}$-Fl | HGEGTFTSDLSK(NIRF)QMEEEAVRLFIEWLKNGGPSSGAPPPS | 39 | K12 | 5311 |

| Abbreviation | Amino Acid sequence | Length (aa) | NiRF mod | MW (kDa) |
|---|---|---|---|---|
| Exendin-4 | HGEGTFTSDLSKQMEEEAVRLFIEWLKNGGPSSGAPPPS | 39 | none | 4188 |
| E4$_{x12}$ | HGEGTFTSDLSXQMEEEAVRLFIEWLKNGGPSSGAPPPS | 39 | X12 | 4155 |
| E4$_{x12}$-VT750 | HGEGTFTSDLSX(PEG-VT750)QMEEEAVRLFIEWLKNGGPSSGAPPPS | 39 | X12(VT750) | 5238 |

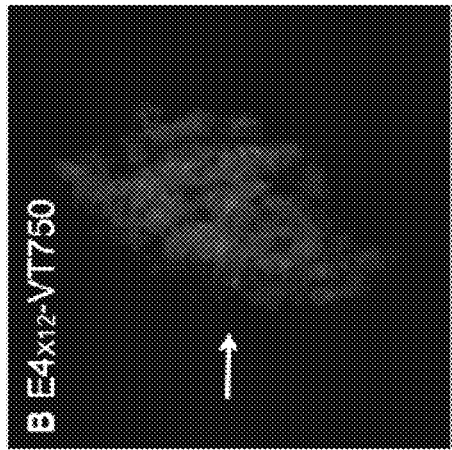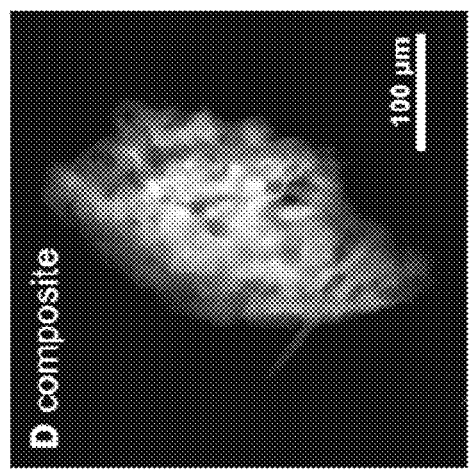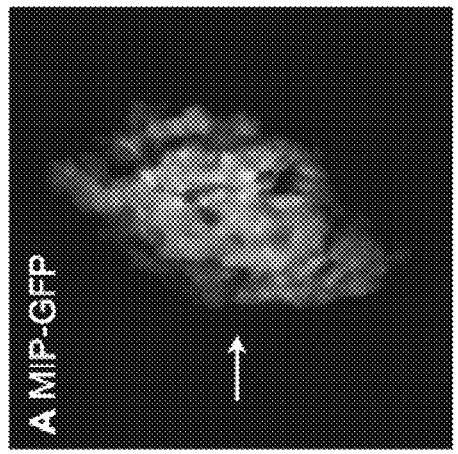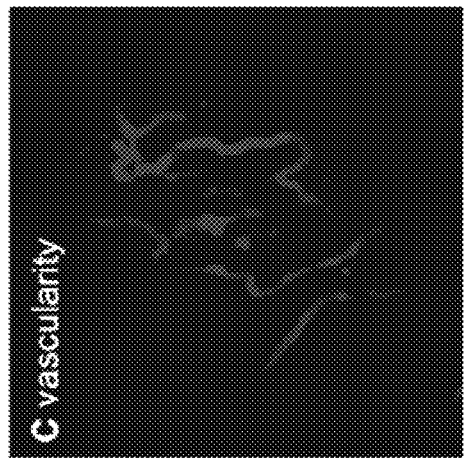

FIG. 11A
FIG. 11B
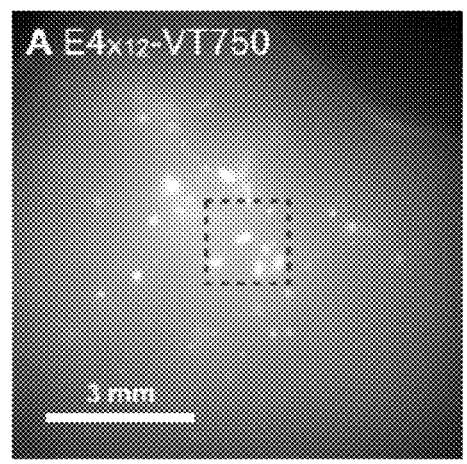
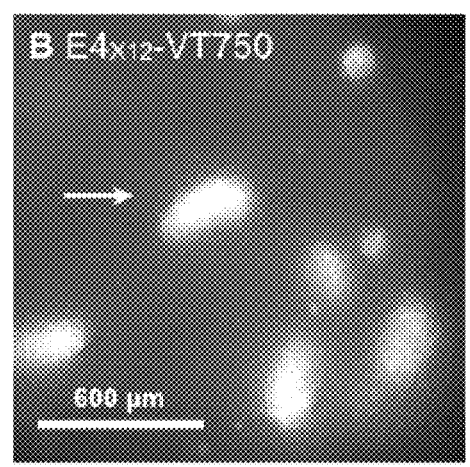
FIG. 11C
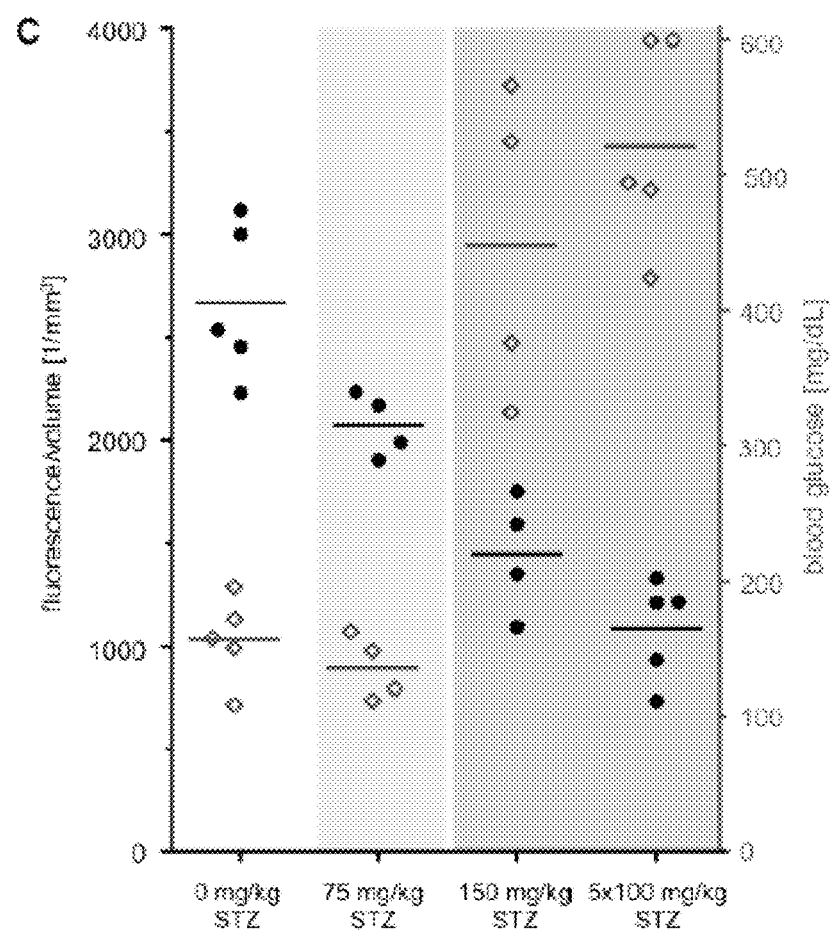

FIG. 13A

| Abbreviation | Amino Acid sequence | Length (aa) | NIRF mod | MW (kDa) |
|---|---|---|---|---|
| Exendin-4 | HGEGTFTSDLSKQMEEEAVRLFIEWLKNGGPSSGAPPPS | 39 | none | 4188 |
| E4$_{C12}$ | HGEGTFTSDLSCQMEEEAVRLFIEWLKNGGPSSGAPPPS | 39 | C12 | 4163 |
| E4$_{Tz12}$ | HGEGTFTSDLSC(Tz)QMEEEAVRLFIEWLKNGGPSSGAPPPS | 39 | Tz12 | 4501 |
| E4$_{TzTCO12}$-$^{19}$F | HGEGTFTSDLSC(TzTCO-$^{19}$F)QMEEEAVRLFIEWLKNGGPSSGAPPPS | 39 | TzTCO-$^{19}$F | 4642 |
| E4$_{TzTCO12}$-$^{18}$F | HGEGTFTSDLSC(TzTCO-$^{18}$F)QMEEEAVRLFIEWLKNGGPSSGAPPPS | 39 | TzTCO-$^{18}$F | 4641 |

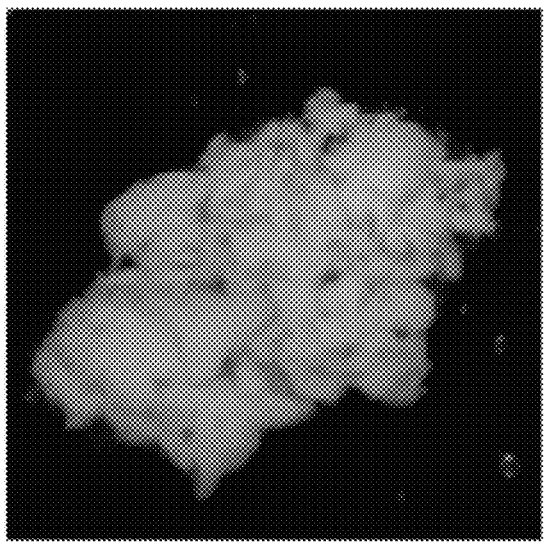
FIG. 16A  A MIP-GFP
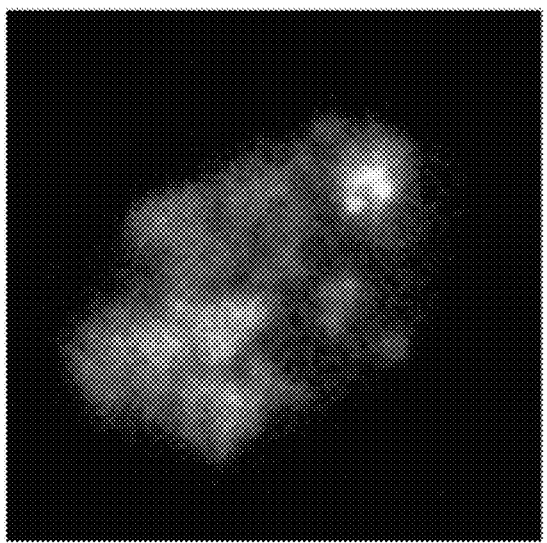
FIG. 16B  B E4-18F
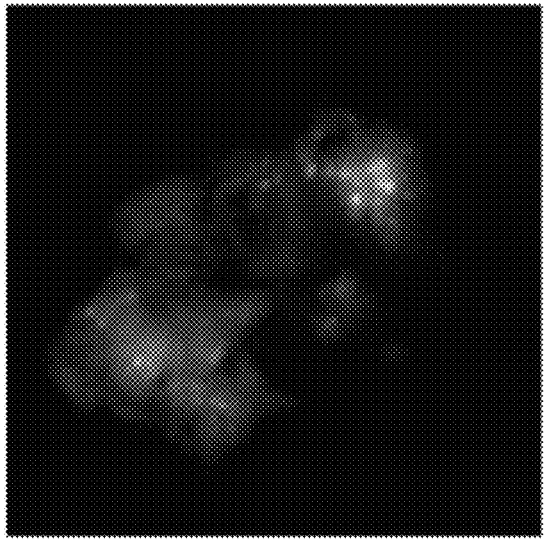
FIG. 16C  C white light

IMAGING BETA CELL MASS

CROSS REFERENCE TO RELATED APPLICATION

This application is continuation of U.S. patent application Ser. No. 14/003,959, filed Sep. 9, 2013, which is a national stage application under 35 U.S.C. § 371 of PCT/US2011/041986, filed Jun. 27, 2011, and claims priority to U.S. Provisional Patent Application No. 61/450,754, filed on Mar. 9, 2011, each of which is incorporated herein by reference in its entirety.

STATEMENT REGARDING FEDERALLY SPONSORED RESEARCH OR DEVELOPMENT

The present invention was made with government support Under Grant Nos. P01 AI54904, RO1 67536, U24 CA092782, and 1RL9EB008539-01 awarded by the National Institutes of Health. The United States Government has certain rights in the invention.

TECHNICAL FIELD

The present disclosure describes the design and synthesis of peptide-detectable agent conjugates for imaging beta cell mass.

BACKGROUND

Beta cell mass (BCM) and the functional state of islets are critical measures in assessing the magnitude of autoimmune destruction in type 1 diabetes (T1D). Progressive loss of BCM is also responsible for the secondary failure of clinical drugs in type 2 diabetes. Serum tests such as insulin/C-peptide do not reliably measure BCM, and currently the only accepted gold standard of measurement is autopsy. Targeting receptors located on beta cells, such as the glucagon like peptide-1 receptor (GLP-1R), could prove useful as a diagnostic, preventative, and clinical tool in assessing beta cell mass. Thus, there exists a need for imaging probes that can be used to: a) better understand the history of the islet and the pathophysiology of diabetes, b) enable earlier diagnosis of T1D, c) allow monitoring of therapeutic efficacy and durability of drugs, d) reveal image-able biomarkers useful in the discovery of new therapies, e) monitor islet transplantation, and e) be used to localize beta cell derived malignancies. The compositions and methods described herein address these and other needs.

SUMMARY

The present disclosure provides, inter alia, compositions and methods of making and using peptide-detectable agent conjugates that can be used to image beta cell mass in vivo and ex vivo. The imaging of beta cell mass can be useful for measuring disease onset, progression and treatment. The peptide-detectable agent conjugates include a detectable agent, a peptide, and a linker that connects the detectable agent to the peptide. The peptide-detectable agent conjugates strongly bind to GLP-1R receptors with high specificity and thus provides a way of directly measuring beta cell mass. The detectable agent can be detected by various imaging modalities including, e.g., near infrared (NIR), single photon emission computed tomography (SPECT) scan, positron emission tomography (PET) scan, or magnetic resonance imaging (MRI) scan or other imaging modality.

Accordingly, in a first aspect the present disclosure provides a composition comprising the peptide sequence SEQ ID NO: 1, wherein the lysine at position 12 is modified with a detectable agent either directly or via a linker.

In some embodiments, the lysine at position 12 is modified with a fluorophore. In some embodiments, the fluorophore is VT-680 or VT-750.

In another aspect, the present disclosure provides a composition comprising the peptide sequence SEQ ID NO:2, wherein the amino acid at position 12 is an unnatural amino acid.

In some embodiments, the unnatural amino acid is selected from the group consisting of: 3-azido-L-alanine, 3-azido-D-alanine, 4-azido-L-homoalanine, 4-azido-D-homoalanine, (S)-2-amino-5-azidopentanoic acid, (R)-2-amino-5-azidopentanoic acid, (S)-2-amino-6-azidohexanoic acid, (R)-2-amino-6-azidohexanoic acid, 4-azido-L-phenylalanine, 4-azido-D-phenylalanine, L-propargylglycine, D-propargylglycine, (S)-2-amino-4-pentynoic acid, (R)-2-amino-4-pentynoic acid, (D)-homopropargylglycine, and (L)-homopropargylglycine.

In some embodiments, the unnatural amino acid is (S)-2-amino-4-pentynoic acid. In some embodiments, the unnatural amino acid is attached to a detectable agent.

In some embodiments, the detectable agent is attached to the unnatural amino acid through the use of a bioorthogonal conjugation reaction.

In some embodiments, the bioorthogonal conjugation reaction is a copper catalyzed "click" cycloaddition reaction or an inverse electron demand Diels-Alder cycloaddition reaction.

In some embodiments, the bioorthogonal conjugation reaction is the copper catalyzed "click" cycloaddition reaction.

In some embodiments, the conjugation reaction between peptide and linker or linker and detectable agent can be a nucleophilic substitution, a maleimide/cysteine reaction, ligation of an azide to a terminal alkyne, strained alkynes or triaryl phosphines, ligation of an aldehyde or ketone to a hydroxylamine or hydrazide. For additional examples of chemical modifications, conjugation strategies and bioorthogonal reactions see, e.g., Beatty, *Acc. Chem. Res.* DOI: 10.1039/C1MB05040K; Sletten et al., *Angew. Chem. Int. Ed.* 48:6974-6998, 2009.

In another aspect, the present disclosure provides a composition comprising the peptide sequence SEQ ID NO:3, wherein the amino acid at position 12 is cysteine.

In some embodiments, the cysteine is modified with a linker comprising a maleimide at a first end and a tetrazine at a second end.

In some embodiments, the cysteine reacts with the maleimide via a 1,2-addition reaction.

In some embodiments, the tetrazine reacts with a strained alkene attached to a detectable agent via an inverse electron demand Diels-Alder reaction.

In some embodiments, the strained alkene is trans-cyclooctene. In some embodiments, the strained alkene is norbornene.

In some embodiments, the strained alkene is trans-cyclooctene.

In some embodiments, the detectable agent comprises a fluorophore, a luminescent agent, a radioactive isotope, or a paramagnetic element.

In some embodiments, the detectable agent is a fluorophore. In some embodiments, the fluorophore is VT-680 or VT-750.

In some embodiments, the detectable agent comprises a radioactive isotope selected from the group consisting of: fluorine-18, carbon 11, nitrogen-13, zirconium-89, copper-64 gallium-67, technetium-99m, indium-111, iodine-123, xenon-133, and thallium-201 or other isotopes suitable for PET and/or SPECT imaging. In some embodiments, the detectable agent is fluorine-18.

In another aspect, the present disclosure provides methods of imaging beta cells in a subject, the method comprising: administering to the subject a peptide-detectable agent conjugate comprising the composition of any one of claims 1 to 12; and detecting the peptide-detectable agent conjugate in the subject; thereby obtaining an image of the peptide-detectable agent conjugate in the subject.

In some embodiments, the methods described herein further comprise quantifying the peptide-detectable agent conjugate in the subject, thereby quantifying beta cell mass.

In some embodiments, the methods described herein further comprise administering the peptide-detectable agent conjugate to the subject a second time, obtaining a second image, and comparing the two images to detect changes in beta cell mass.

In some embodiments, the methods described herein further comprise administering a treatment to the subject before the second time, wherein a change in the two images indicates an effect of the treatment on beta cell mass.

In some embodiments, the subject has a beta cell tumor, and the treatment is chemotherapy or surgery. In some embodiments, the tumor is an insulinoma. In some embodiments, the subject has diabetes or is pre-diabetic, and the treatment is intended to increase beta cell mass. In some embodiments, the treatment is a beta cell regeneration treatment. In some embodiments, the treatment is part of a clinical trial.

In some embodiments, the image is obtained by an imaging modality selected from the group consisting of: X-ray imaging, computed tomography (CT) imaging, single photon emission computed tomography (SPECT) imaging, positron emission tomography (PET) imaging, infrared imaging, magnetic resonance imaging (MRI), fluorescence imaging, laparoscopy, and endomicroscopy.

In some embodiments, the detectable agent is paramagnetic or radioactive. In some embodiments, the detectable agent comprises a radioactive isotope selected from the group consisting of: fluorine-18, carbon 11, nitrogen-13, zirconium-89, copper-64 gallium-67, technetium-99m, indium-111, iodine-123, xenon-133, and thallium-201 or other isotopes suitable for PET and/or SPECT imaging. In some embodiments, the detectable agent is fluorine-18.

By virtue of their design, the peptide-detectable agent conjugates described herein possess certain advantages and benefits. First, the peptide-detectable agent conjugates can be used to better understand beta cell related illnesses such as type 1 diabetes. Second, the conjugates provide a very sensitive method of detecting pre-diabetes while the disease is still in the occult phase. Because these conjugates specifically bind the GLP-1R in beta cells, these conjugates can detect beta cell loss, which is an early indicator that a subject is either pre-diabetic and/or at risk of developing diabetes. Third, these conjugates can be used to monitor the efficacy, toxicity, and durability of beta cell loss treatments during clinical trials. Also, because these conjugates can be used in clinical trials, they can facilitate the discovery of new therapies.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

DESCRIPTION OF DRAWINGS

FIG. 1A is a table depicting the amino acid sequences and molecular weight of synthesized fluorescent Exendin-4 conjugates.

FIGS. 9A-9D are intravital confocal images of a pancreatic islet (arrows) in a live MIP-GFP mouse. FIG. 9A is an image of the GFP signal from MIP-GFP-positive pancreatic beta cells; FIG. 9B is an image of Exendin-4$_{X12}$-VT750 (0.2 nmol/g); FIG. 9C is a fluorescence image of a vascular agent; and FIG. 9D is a composite of the images depicted in FIGS. 9A-9D. All images were acquired with a 20× objective in anesthetized live mice.

FIGS. 11A and 11B are surface reflectance microscopy images of typical staining patterns observed for pancreata injected with Exendin-4$_{X12}$ conjugated to VT750 (0.1 nmol/g, 40 minutes, mouse perfused and pancreas flushed); and FIG. 11B is an image of a higher magnification of a section from FIG. 11A.

FIG. 11C is an image of quantitative fluorescence signals (750 nm) observed in pancreata of diabetic and non-diabetic mice injected with Exendin-4$_{X12}$-VT750 (0.1 nmol/g, 40 minutes, mouse perfused and pancreas flushed; P<0.0001). Light grey: STZ treated but non-diabetic mice (blood glucose levels <200 mg/dL). Darker grey: overt diabetic (blood glucose levels >300 mg/dL). Blood glucose levels are indicated by 0 symbols (P<0.0001).

FIG. 13A is a table of the amino acid sequences and molecular weight of synthesized Exendin-4 in which the lysine at position 12 has been replaced with cysteine (second row), then modified with a linker having a tetrazine (E4$_{Tz12}$) (third row), and then conjugated to an $^{19}$F isotope (E4$_{TzTCO12}$-$^{19}$F) (fourth row), and also conjugated to an $^{18}$F radioactive isotope (E4$_{TzTCO12}$-$^{18}$F) (bottom row).

FIG. 16A is a fluorescence image of the pancreas of a MIP-GFP mouse injected with 50 μCi of Exendin-4 conjugated to 18F. FIG. 16A is a GFP reflectance image; FIG. 16B is an autoradiography image; and FIG. 16C is a white field image.

DETAILED DESCRIPTION

The present invention provides compositions and methods for imaging beta cell mass ex vivo and in vivo, which include a detectable agent, a peptide, and a linker that connects the detectable agent to the peptide. The peptide can be a derivative of Exendin-4 that has been modified at the 12 position to allow for the attachment of a detectable agent. The peptide-detectable agent conjugates can then be imaged in vivo or ex vivo using known imaging modalities. For example, the peptide-detectable agent conjugates described herein exhibit high beta cell specificity within the pancreas in vivo. Thus, these peptide-detectable agent conjugates can be used to noninvasively image the whole pancreas by detecting the accumulation of the peptide-detectable agent conjugates in beta cells. These peptide-detectable agent conjugate can be detected, e.g., by NIR, SPECT, PET, or MRI, and facilitate the noninvasive detection of beta cell mass changes. In vivo, these peptide-detectable agent conjugates can also be imaged using laparoscopic imaging and endomicroscopy.

Peptide-Detectable Agent Conjugates

Figure 1B:
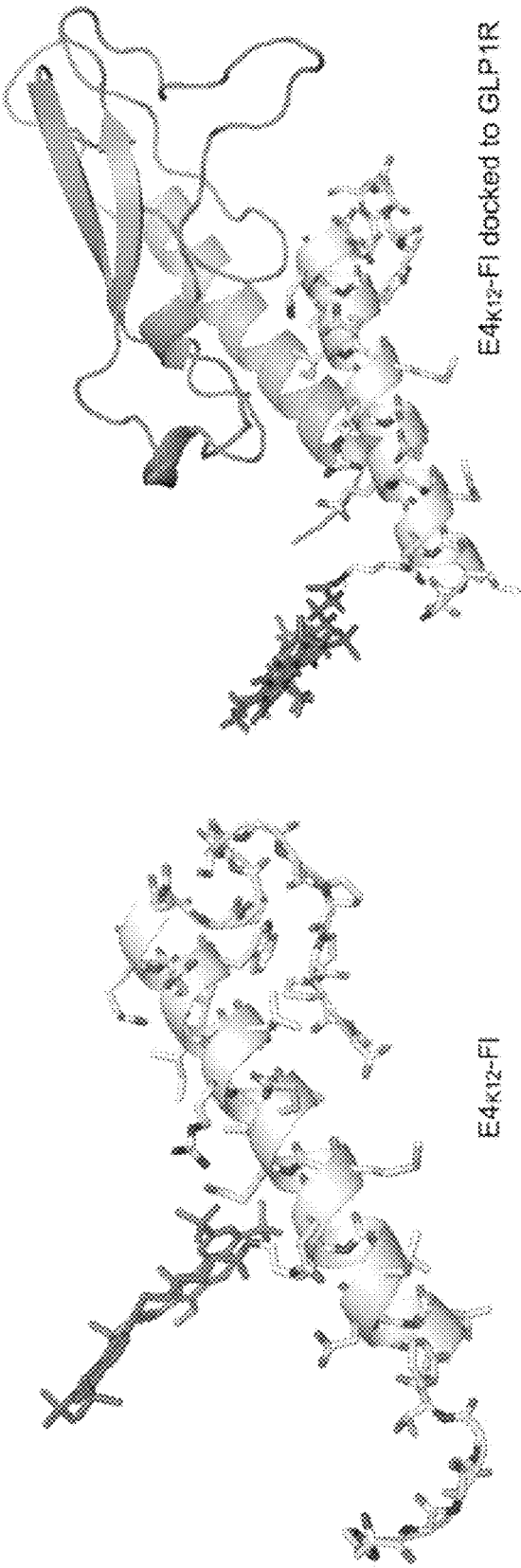
FIG. 1B is a schematic of Exending-$4_{K12}$-VT-680 based on the nuclear magnetic resonance structure (NMR) (left); and a molecular model of Exendin-$4_{K12}$-VT680 complexed with the extracellular domain of GLP-1R based on the crystal structure.

The peptide-detectable agent conjugates include a detectable agent, an Exendin-4 derived peptide, and a linker that connects the detectable agent to the peptide (see FIG. 1A). The peptide can be modified at the lysine of position 12 either by replacing the lysine with a natural amino acid, or by replacing the lysine-12 with an unnatural amino acid. The natural or unnatural amino acid can then be further modified with a linker that can facilitate the attachment of a detectable agent.

Exendin-4 Derivatives

In some embodiments, the lysine at position 12 of Exendin-4 can be replaced by another amino acid. In some embodiments, the lysine at position 12 of Exendin-4 can be chemically modified to attach a linker. This linker can have a detectable agent attached to it or the linker can be further reacted to attach a detectable agent.

Replacement of Lysine-12 of Exendin-4

Figure 17:
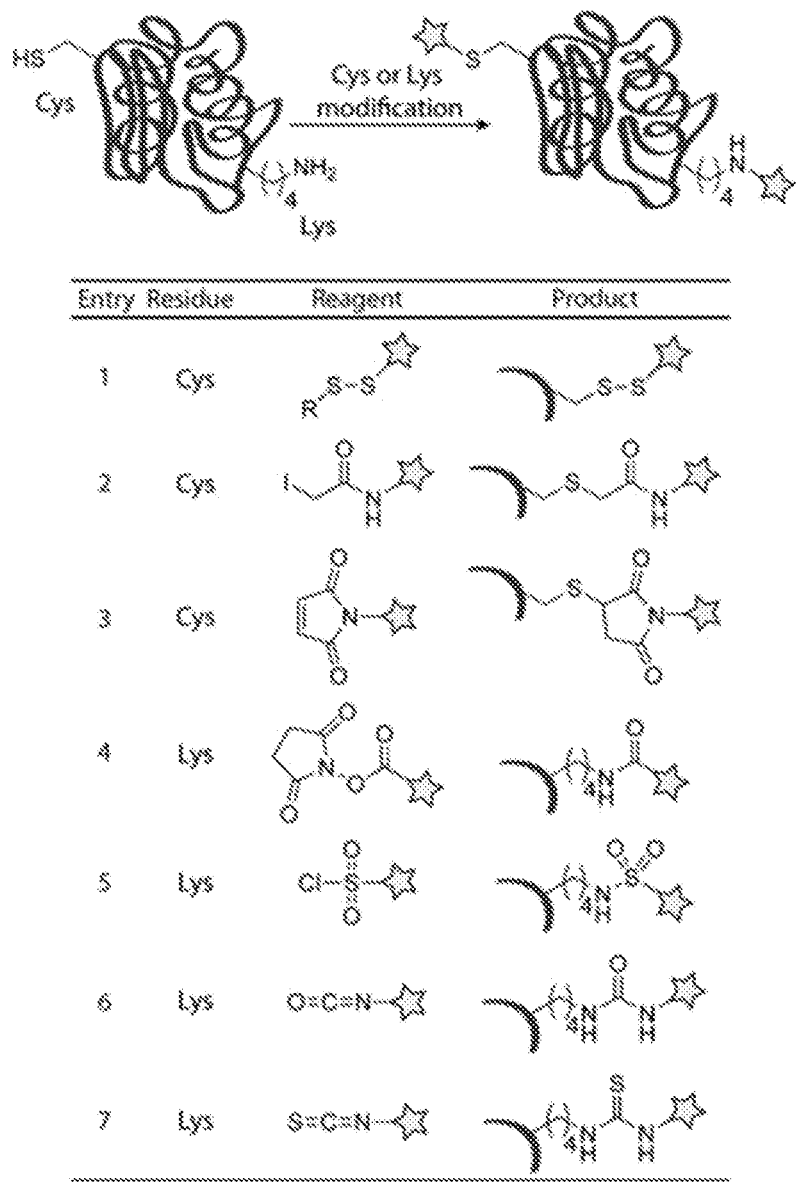
FIG. 17 shows chemical modification to cysteine or lysine at position 12 of Exendin-4.

In some embodiments, the lysine at position 12 of Exendin-4 can be replaced with a cysteine. In some embodiments, the thiol group on the cysteine can be chemically modified to attach a detectable linker (see entries 1-3 of FIG. 17). In some embodiments, the thiol group can first be chemically modified to attach a linker, and then further modified to attach another group containing the detectable agent. For example, the thiol group of cysteine can undergo disulfide exchange to form mixed disulfides as well as alkylation with alkyl halides or Michael addition with α,β-unsaturated carbonyl compounds to yield thioethers.

In some embodiments, the lysine at position 12 of Exendin-4 can be replaced with a tyrosine. The phenol moiety of tyrosine can be modified through electrophilic aromatic substitution reactions with diazonium salts, iodine, or nitrous acid.

Other examples can include replacing lysine-12 with glutamate and aspartate residues and then modifying the amines located on glutamate and aspartate via carbodiimides. Additionally, lysine-12 can be replaced with histidine and can then be modified with pyrocarbonates.

In other embodiments, lysine-12 can be replaced with azides or alkynes and then be modified with alkynes or azides.

In other embodiments, lysine-12 can be replaced with strained alkynes or azides and then modified with azides or strained alkynes.

In other embodiments, lysine-12 can be replaced with azides or triaryl phosphines and then modified with triaryl phosphines and azides (Staudinger ligation).

In other embodiments, lysine-12 can be replaced with tetrazines or strained alkenes and then modified with strained alkenes or tetrazines.

In other embodiments, lysine-12 can be replaced with tetrazoles or alkenes and then reacted with alkenes or tetrazoles using a 1,3-dipolar cycloaddition.

In other embodiments, lysine-12 can be replaced with an alkene and then reacted with other alkenes using cross metathesis reactions.

For additional examples of chemical modifications, conjugation strategies and bioorthogonal reactions see, e.g., Beatty, *Acc. Chem. Res.* DOI: 10.1039/C1MB05040K; Sletten et al., *Angew. Chem. Int. Ed.* 48:6974-6998, 2009.

Chemical Modification of Existing Lysine-12 of Exendin-4

In some embodiments, the existing Lysine at position 12 of Exendin-4 is not replaced but instead reacted with activated esters, sulfonyl chlorides, isocyanates, or isothiocyanates to afford amides, sulfonamides, ureas, or thioureas, respectively (see entries 4-7 in FIG. 17) to provide a moiety for attachment of the detectable agent. Lysine residues can also undergo reductive amination reactions with aldehydes to form secondary or tertiary amines (see FIG. 17). For additional examples of chemical modifications to amino acids see, e.g., Sletten, et al. *Angew. Chem. Int. Ed.* 48: 6974-6998, 2009; Glazer, et al. *Annu. Rev. Biochem.* 39: 101, 1970; M. B. Francis in *Chemical Biology* (Eds.: S. L. Schreiber, T. Kapoor, G. Wess), Wiley-VCH, Weinheim, p. 593, 2007; S. D. Tilley, N. S. Joshi, M. B. Francis in *The Wiley Encyclopedia of Chemical Biology* (Ed.: T. Begley), Wiley-VCH, Weinheim, 2008; G. T. Hermanson, Bioconjugate Techniques, 1st ed., Academic Press, San Diego, Calif., 1996, all of which have been incorporated by reference in their entireties.

Unnatural Amino Acids

In some embodiments, the lysine at position 12 is replaced with an unnatural amino acid that may already possesses a chemical group that can react in a bioorthogonal conjugation reaction, e.g., the copper catalyzed "click" reaction or the inverse electron demand hetero-Diels Alder reaction. For example, the unnatural amino acid can have a reactive group that can react via a bioorthogonal conjugation reaction with a reactive group located on a linker attached to a detectable agent. In some embodiments, the unnatural amino acid has an azide and the linker has an alkyne, and the azide and the alkyne are reactive partners for the copper catalyzed "click" reaction. Alternatively, the alkyne is located on the unnatural amino acid and the azide is located on the linker attached to the detectable agent. Exemplary unnatural amino acids that can participate in the copper catalyzed "click" reaction are described in the Iris Biotech GMBH catalog that can be found at 2.imimg.com/data2/BB/AF/MY-2981732/iris-biotech-gmbh.pdf.

Linker

In some embodiments, a linker can be attached to the amino acid or unnatural amino acid. The term "linker" as used herein refers to a group of atoms, e.g., 0-50000 atoms, and can be comprised of the atoms or groups of atoms such as, but not limited to, hydrogen and carbon, e.g, methylene (—CH₂—), amino, amido, alkylamino, oxygen, sulfur, sulfoxide, sulfonyl, carbonyl, and imine. The linker can also comprise part of a saturated, unsaturated or aromatic ring, including polycyclic and heteroaromatic rings wherein the heteroaromatic ring is an aryl group containing from one to four heteroatoms, N, O or S. Specific examples include, but are not limited to, unsaturated alkanes, polyethylene glycols, and dextran polymers or dendrimers. The linker must not interfere with the imaging methods or with the bioorthogonal conjugation reactions described herein.

In some embodiments, the linker is not linear. For example, the linker can be a crosslinked polymer, biopolymer or dendrimer or nanoparticle, allowing attachment of one or more peptides to one or more detectable agents increasing the affinity of the peptide via multivalency, increasing the half-life, and allowing larger loading of detectable agents, which do not necessarily have to be identical and can be used to visualize beta cell mass or insulinomas with multiple imaging modalities.

Figures 13B, 13C:
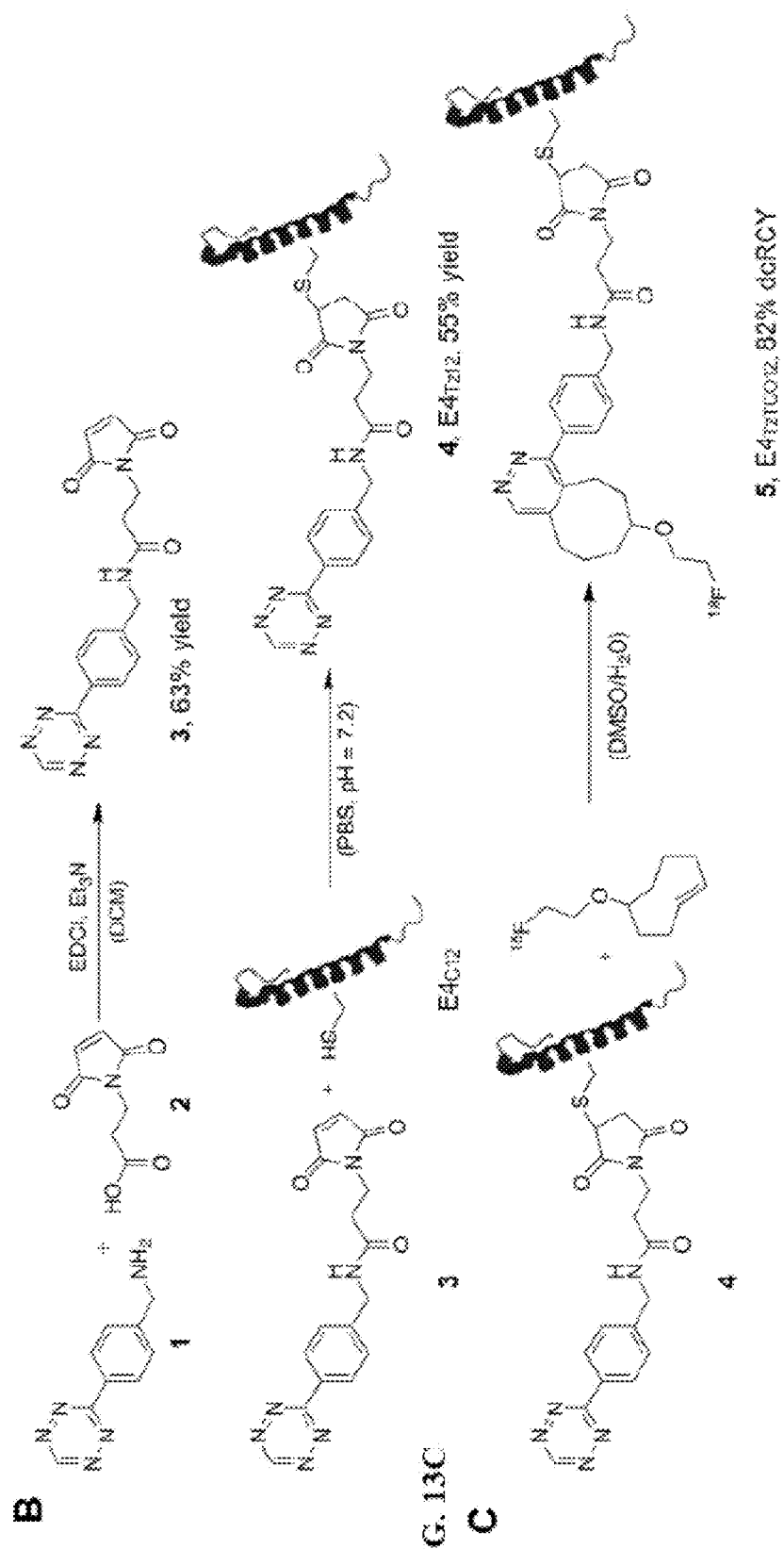
FIG. 13B is a synthetic scheme of the preparation of the linker having a maleimide at a first end and a tetrazine at a second end (3), attachment to the cysteine at position 12 of Exendin-4 (4).
FIG. 13C is the bioorthogonal conjugation of structure 4 with a strained alkene having a $^{18}$F via inverse electron demand Diels-Alder reaction to form the peptide-detectable agent conjugate 5 (E4$_{TzTCO12}$-18F).

In some embodiments, the linker has a first end with a reactive group that can attach to the amino acid or unnatural amino acid. For example, the amino acid can be cysteine and the linker can have a maleimide at the first end that reacts with the thiol on the cysteine via 1,2-addition (Michael Reaction) to form a carbon-sulfur bond (see FIG. 17, entry 3). The linker can have a second end that has a detectable agent already attached to the linker. Alternatively, the second end of the linker can further be coupled with a reactive group which is part of the detectable agent moiety. This coupling reaction can occur via a bioorthogonal conjugation reaction, e.g. a copper catalyzed "click" reaction or an inverse electron demand Diels-Alder cycloaddition, as described herein. In some embodiments, the cysteine can react with a linker that has a maleimide at a first end of the linker to form a carbon-sulfur bond between the thiol group of the cysteine residue and the linker. The linker can have a tetrazine located on the second end. This tetrazine can then react, via an inverse electron demand Diels-Alder cycloaddition, with a strained alkene attached to a detectable agent. See, e.g. FIGS. 13B and 13C.

In some embodiments, the first end of the linker can have an activated ester, e.g., an NHS-ester, which can form an amide bond with the amino group of the existing lysine residue at position 12. The detectable agent can be located on the second end of the linker. In some embodiments, the first end of the linker can have an azide, which can react with the alkyne group of the unnatural amino acid, (S)-2-amino-4-pentynoic acid at position 12 of Exendin-4, via a copper-catalyzed "click" reaction, and the detectable agent can be located at the second end of the linker. See, e.g., FIG. 3B.

Bioorthogonal Conjugation of Amino Acid to Detectable Agent

Inverse Electron Demand Diels-Alder Reaction

The compositions and methods described herein include the use of bioorthogonal conjugation reactions such as the inverse electron demand Diels-Alder reaction. This reaction employs a diene and a dienophile. The reaction of a diene (e.g., a substituted tetrazine) with a dienophile (e.g., an alkene or alkyne), produces an unstable cycloadduct that subsequently undergoes a retro-Diels-Alder cycloaddition reaction to produce dinitrogen as a byproduct and the desired dihydropyrazine (after reaction with an alkene) or pyrazine (after reaction with an alkyne) products (shown below in Scheme 1). See e.g., Sauer et al., Chem Ber 998: 1435-1445, 1965, which is incorporated by reference in its entirety. The dihydropyrazine product may undergo an additional oxidation step to generate the corresponding pyrazine.

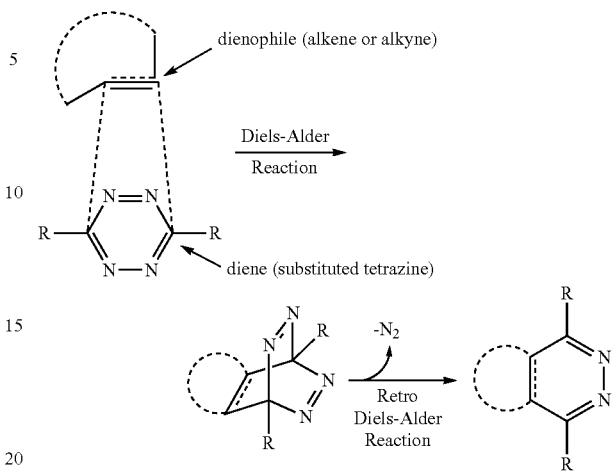

Scheme 1

A variety of tetrazines and dienophiles including cyclic and linear alkenes or alkynes have been studied in this reaction. Selection of the appropriate reaction partners, allows for tuning of the coupling rate by several orders of magnitude. (Balcar J et al., 1983, Tet Lett 24:1481-1484; Thalhammer F et al., 1990, Tet Lett 47:6851-6854). See also US 2006/0269942, WO 2007/144200, and US 2008/0181847. Bioconjugation methods using inverse electron demand Diels-Alder cycloadditions between tetrazines and highly strained dienophiles such as norbornene and trans-cyclooctene are known in the literature, however the tetrazine used has limited stability to aqueous media. (Blackman et al., 2008, J Am Chem Soc, 130, 13518-9; Devaraj et al., 2009, Angew Chem Int Ed Engl, 48, 7013-6; Devaraj et al. Bioconjug Chem, 19: 2297-9, 2008; Pipkorn et al., J Pept Sci, 15, 235-41, 2009).

In some embodiments, the detectable agent carries a functional group such as an amine, alcohol, carboxylic acid or ester, or other group of atoms that can undergo a chemical reaction allowing attachment to the diene or dienophile. Alternatively or in addition, the dienophile or heterodienophile (which can be, e.g., an alkene, alkyne, nitroso, carbonyl or imine) possesses a reactive functional group for attachment to the detectable agent. Thus, the reactive functional group on the detectable agent and/or diene/dienophile undergoes a chemical reaction to form a link between the detectable agent and the diene or dienophile.

In some embodiments, the diene or dienophile can be incorporated into a non-natural amino acid as the side chain. One of skill in the art could readily synthesize such compounds. For example, the side chain of phenylalanine or tyrosine could be replaced with a diene, e.g., a tetrazine; a dienophile, e.g., a trans-cyclooctene or norbornene, which can replace the side chain of phenylalanine, tyrosine, isoleucine, leucine, or tryptophan. These new unnatural amino acids can then be used similarly to known non-natural amino acids, e.g., a peptide or protein can be produced that include the diene or dienophile already incorporated into the primary structure of the peptide or protein.

Dienes

In some embodiments, the diene can be a substituted tetrazine or other heteroaromatic ring system with at least two nitrogens adjacent to each other, and which is a highly reactive participant in the inverse electron demand Diels-Alder reaction. The diene can be linked to the amino acid or unnatural amino acid through the use of a linker. In this embodiment, the diene possesses a reactive group such as an amine, alcohol, carboxylic acid, ester, or activated ester, or other group that can undergo a chemical reaction with the reactive moiety on the amino acid or unnatural amino acid to form a link between the two. For example, the thiol group of a cysteine at position 12 of Exendin-4 can undergo a 1,2-addition reaction with a linker having a maleimide at the first end to install a linker onto the cysteine group. The linker at the second end can have a tetrazine moiety ready for reaction with a dienophile located on the detectable agent (see FIG. 13B, compound 4). Dienes useful in the present disclosure include but are not limited to aromatic ring systems that contain two adjacent nitrogen atoms, for example, tetrazines, pyridazines, substituted or unsubstituted 1,2-diazines. Other 1,2-diazines can include 1,2-diazines annelated to a second π-electron-deficient aromatic ring such as pyrido[3,4-d]pyridazines, pyridazino[4,5-d] pyridazines, and 1,2,4-triazines. Pyridazines can also be fused with a five-membered heterocycle such as imidazo[4,5-d]pyridazines and 1,2,3-triazolo[4,5-d]pyridazines. In some preferred embodiments, the diene is an asymmetrical tetrazine as described herein, e.g., 3-(p-Benzylamino)-1,2,4,5-tetrazine (Structure I).

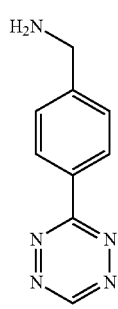

Structure I

Dienophiles

Dienophiles useful in the present methods and compositions include but are not limited to carbon containing dienophiles such as alkenes or alkynes, or compounds containing nitroso, carbonyl or imine groups. In some embodiments, the dienophile is a strained dienophile. As used herein, a "strained" dienophile has a dihedral angle that deviates from the idealized 180 degree dihedral angle. Alternatively, non-strained dienophiles (e.g., sytrenes) and/ or electron rich electrophiles (e.g., eneamines or vinyl ethers), can also be used with nitroso compounds. Alkenes as used herein refer to an alkyl group having one or more double carbon-carbon bonds such as an ethylene, propylene, and the like. Alkenes can also include cyclic, ring-strained alkenes such as trans-cyclooctene or norbornene carrying a double bond which induces significant ring strain and is thus highly reactive. Alkenes can also include more complex structures such as indoles and azaindoles, electron rich enamines. Heterodienophiles containing carbonyl, nitroso or imine groups can also be used. In some embodiments, the dienophile is a trans-cyclooctenol, e.g., (E)-cyclooct-4-enol.

In some embodiments, the detectable agent is chemically attached to the dienophile. For example, the strained alkene is chemically coupled to a detectable agent, e.g., a trans-cyclooctene modified with a radioactive isotope, e.g., $^{18}F$ (see Structure II below).

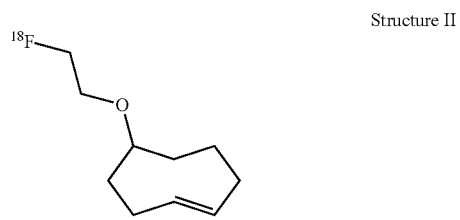 [SMILES: [18F]CCOC1CC/C=C/CCC1]

Structure II

Copper Catalyzed "Click" Reactions

The compositions and methods described herein also include the use of copper catalyzed "click" reaction pairs that include an azide and an alkene. In other embodiments, the compositions and methods described herein can also include the use of an aza-ylide and an ester, i.e., Staudinger ligation. See, e.g. Prescher et al., Nature 430(7002): 873-877, 2004; Rostovtsev et al., Angew Chem Int Ed 41(14): 2596-2599, 2002. Bioorthogonal "click" chemistries which may require catalysts or might be catalyst free are widely used in chemical biology for a myriad of applications such as activity based protein profiling, crosslinking of proteins, monitoring cell proliferation, generation of novel enzyme inhibitors, monitoring the synthesis of newly formed proteins, protein target identification, and studying glycan processing.

Other examples include the use of "click" chemistry to increase the signal of the detectable agent. A number of elegant probes have been introduced whose fluorescence increases after azide-alkyne cycloaddition, tetrazine-trans-cyclooctene, inverse electron demand cycloaddition, or for example staudinger ligation coupling reactions (Sivakumar et al., 2004, Org Lett, 6, 4603-6; Zhou and Fahrni, 2004, J Am Chem Soc, 126, 8862-3; Hangauer and Bertozzi, 2008, Angew Chem Int Ed Engl, 47, 2394-7; Lemieux et al., 2003, J Am Chem Soc, 125, 4708-9; Devaraj et al., 2010, Angew Chem Int Ed Engl). Most, but not all of these strategies either require a reactive group intimately attached to the fluorophore or take advantage of a FRET based activation requiring appendage of an additional molecule that can act as an energy transfer agent.

Detectable Agents

Examples of detectable agents include various organic small molecules, inorganic compounds, nanoparticles, enzymes or enzyme substrates, fluorescent materials, luminescent materials, bioluminescent materials, chemiluminescent materials, radioactive materials, and contrast agents. Examples of suitable enzymes include horseradish peroxidase, alkaline phosphatase, beta-galactosidase, or acetylcholinesterase; examples of suitable fluorescent materials include boron-dipyrromethene (BODIPY®), 4,4-difluoro-5,7-dimethyl-4-bora-3a,4a-diaza-s-indacene-3-propionic acid (BODIPY® FL), 6-((4,4-difluoro-1,3-dimethyl-5-(4-methoxyphenyl)-4-bora-3a,4a-diaza-s-indacene-2-propionyl)amino)hexanoic acid, succinimidyl ester (BODIPY® TRM-X), Oregon Green 88, 6-(((4,4-difluoro-5-(2-pyrrolyl)-4-bora-3a,4a-diaza-s-indacene-3-yl)styryloxy)acetyl) aminohexanoic acid, succinimidyl ester (BODIPY® 650/ 665-X), 7-N,N-diethylaminocoumarin, VIVOTAG 680 (an amine-reactive near-infrared fluorochrome, from VisEn Medical), VIVOTAG-S 750 (VT750-NHS ester), umbelliferone, fluorescein, fluorescein isothiocyanate, rhodamine, dichlorotriazinylamine fluorescein, dansyl chloride or phycoerythrin.

Examples of luminescent materials include luminol. Examples of bioluminescent materials include luciferase, luciferin, and aequorin.

Examples of suitable radioactive material include $^{18}F$, $^{67}Ga$, $^{81m}Kr$, $^{82}Rb$, $^{111}In$, $^{123}I$, $^{133}Xe$, $^{201}Tl$, $^{125}I$, $^{35}S$, $^{14}C$, or $^{3}H$, $^{99m}Tc$ (e.g, as pertechnetate (technetate(VII), $TcO_4^-$) either directly or indirectly, or other radioisotope detectable by direct counting of radioemmission or by scintillation counting.

In addition, contrast agents, e.g., contrast agents for MRI or NMR, for X-ray CT, Raman imaging, optical coherence tomogrpahy, absorption imaging, ultrasound imaging, or thermal imaging can be used. Exemplary contrast agents include gold (e.g., gold nanoparticles), gadolinium (e.g., chelated Gd), iron oxides (e.g., superparamagnetic iron oxide (SPIO), monocrystalline iron oxide nanoparticles (MIONs), and ultrasmall superparamagnetic iron oxide (USPIO)), manganese chelates (e.g., Mn-DPDP), barium sulfate, iodinated contrast media (iohexol), microbubbles, or perfluorocarbons can also be used.

In some embodiments, the detectable agent is a non-detectable pre-cursor that becomes detectable upon activation. Examples include fluorogenic tetrazine-fluorophore constructs (e.g., tetrazine-BODIPY FL, tetrazine-Oregon Green 488, or tetrazine-BODIPY TMR-X) or enzyme activatable fluorogenic agents (e.g., PROSENSE (VisEn Medical))

When the compounds are enzymatically labeled with, for example, horseradish peroxidase, alkaline phosphatase, or luciferase, the enzymatic label is detected by determination of conversion of an appropriate substrate to product.

In vitro assays in which these compositions can be used include enzyme linked immunosorbent assays (ELISAs), immunoprecipitations, immunofluorescence, enzyme immunoassay (EIA), radioimmunoassay (RIA), and Western blot analysis.

Using the Peptide-Detectable Agent Conjugates
Methods of Detecting Peptide-Detectable Agent Imaging Conjugates The peptide-detectable imaging conjugates described herein can be imaged using methods known in the art. For example, imaging can be achieved in living animals, organs, or tissues, using e.g. near infrared (NIR), MR imaging (MRI), positron emission tomography (PET), single photon computerized tomography (SPECT), or other whole body imaging modalities. The detectable agent of the peptide-detectable agent imaging conjugate can be imaged by these whole body imaging modalities to detect beta cell mass. For example, these peptide-detectable agent imaging conjugates can be detected by traditional fluorescence imaging techniques allowing for the facile tracking of the peptide-detectable agent imaging conjugates by fluorescence microscopy or flow cytometry using methods known in the art, e.g., as described in US 2005/0249668, the content of which is incorporated by reference in its entirety.

In some embodiments, the peptide-detectable agent conjugates are imaged in vivo using laparoscopy and endomiscroscopy. For example, the use of laparoscopy permits the facile, real-time imaging and localization of tumors labeled with fluorescent proteins. See, e.g. Cao et al. Surgical Endoscopy 25(1): 48-54, 2011, the content of which is incorporated by reference in its entirety. In some embodiments, laparoscopy can be used to diagnose pancreatic cancer by imaging the accumulation of the peptide-detectable agent conjugates on the beta cells. See, e.g., Friess et al. Journal of the American College of Surgeons 186(6): 675-682, 1998, the content of which is incorporated by reference in its entirety. In some embodiments, the use of laparoscopy as an imaging modality can be useful during surgery to locate insulinomas. See, e.g. Fink et al. Journal of Gastrointestinal Surgery 15(7): 1092-7, 2011, the content of which is incorporated by reference in its entirety. In some embodiments, the peptide-detectable agent conjugates can be imaged using fiber optic endomicroscopy. See, e.g. Wu et al. Optics Express 17(10): 7907-7915, 2009; and Bao et al. Optics Express 18(2): 1255-1260 (2010), the contents of which are incorporated by reference in their entireties.

Imaging the Peptide-Detectable Agent Conjugates

The compositions and methods described herein can be imaged using a variety of modalities that are known to one of skill in the art. Detection methods can include both imaging ex vivo and in vivo imaging methods, e.g., immunohistochemistry, bioluminescence imaging (BLI), Magnetic Resonance Imaging (MRI), positron emission tomography (PET), electron microscopy, X-ray computed tomography, Raman imaging, optical coherence tomography, absorption imaging, thermal imaging, fluorescence reflectance imaging, fluorescence microscopy, fluorescence molecular tomographic imaging, nuclear magnetic resonance imaging, X-ray imaging, ultrasound imaging, photoacoustic imaging, lab assays, or in any situation where tagging/staining/imaging is required.

In Vivo Imaging

The compounds and compositions described herein can be used in in vivo imaging methods to detect, quantify and evaluate beta cell mass. In general, such methods include administering to a subject one or more peptide-detectable agent conjugates described herein; optionally allowing conjugate to distribute within the subject; and imaging the subject, e.g., by fluoroscopy, radiography, computed tomography (CT), MRI, PET, SPECT, laparoscopy, endomicroscopy, or other whole body imaging modality to detect the presence of beta cell mass. Furthermore, it is understood that the methods (or portions thereof) can be repeated at intervals to evaluate the subject and detect any changes in beta cell mass over time. Information provided by such in vivo imaging, for example, the presence, absence, or level of emitted signal, can be used to detect and/or monitor the loss of beta cell mass or increase of beta cell mass, e.g., after medical treatment.

A number of preclinical and clinical applications for this specific conjugate can be envisioned. For example, the peptide-detectable agent conjugates described here can be used: 1) for the early detection of insulinomas, a deadly cancer evolving from healthy pancreatic beta cells; and 2) as a diagnostic tool for the early detection of pancreatic beta cell loss (i.e., the presence of an abnormally low beta cell mass), resulting in type 1 diabetes, a disease affecting millions of individuals in the United States of America alone. Early detection of pancreatic beta cell loss will not only improve direct patient care, making it possible to diagnose patients during the state of occult diabetes (before physical symptoms occur), but it will also help to find cures and treatment for diabetic patients, since the effect of drugs on pancreatic beta cell mass can be measured directly.

In addition, in vivo imaging can be used to assess the effect of a compound or therapy on cells expressing GLP1-R, e.g., beta cells, by using the conjugates described herein, wherein the subject is imaged prior to and after treatment with the compound or therapy, and the corresponding signal/images are compared. For example, a subject with a cancer, e.g., an insulinoma, can be imaged prior to and after treatment with chemotherapy or radiation therapy to determine the response of the beta cells or GLP1-R-expressing cancer cells, e.g., insulinomas, to treatment. Example chemotherapy treatments include 5-fluorouracil (5-FU), gemcitabine, and Capecitabine (XELODA®). Other novel small molecules are being widely and actively researched. These compounds are based on classical mechanisms of action as well as biological therapies targeting novel cellular survival pathways, and include fluoropyrimidines, nucleoside cytidine analogues, platinum analogues, topoisomerase inhibitors, antimicrotubule agents, proteasome inhibitors, vitamin D analogues, arachidonic acid pathway inhibitors, histone deacytylator inhibitors, farnesyltransferase inhibitors and epidermal growth factor receptor therapies. See, e.g., Shore et al. *Alimentary Pharmacology & Therapeutics,* 18(11): 1049-1069, 2003. Other examples of chemotherapy treatments include cisplatin, The methods and compositions described herein can be used to help a physician or surgeon to identify and characterize pancreatic diseases, such as diabetes and tumors of the pancreas such as insulinoma. The methods and compositions described herein can also be used in the detection, characterization, and/or determination of the localization of a disease, especially early disease, the severity of a disease or a disease-associated condition, the staging of a disease, and/or monitoring a disease. The presence, absence, or level of an emitted signal can be indicative of a disease state.

In some embodiments, the peptide-detectable agent conjugates can be used to monitor an increase in beta cell mass after treatment. For example, the peptide-detectable agent conjugates can be used to assess the effectiveness of islet transplantation, e.g., where islets are taken from the pancreas of a deceased organ donor. The islets are purified, processed, and transferred into another person. Once implanted, the beta cells in these islets begin to make and release insulin. See, e.g., the worldwide web page diabetes.niddk.nih.gov/dm/pubs/pancreaticislet/ for a description of islet transplantation. These peptide-detectable agent conjugates could be useful in monitoring beta cell mass increase after transplantation.

In Vitro Imaging

With respect to in vitro imaging methods, the compounds and compositions described herein can be used in a variety of in vitro assays. An exemplary in vitro imaging method comprises: contacting a sample, for example, a biological sample, with one or more peptide-detectable agent conjugates; allowing the conjugate(s) to interact with a biological target in the sample; optionally, removing unbound agents; illuminating the sample with light of a wavelength absorbable by a fluorophore of the agents; and detecting a signal emitted from fluorophore thereby to determine whether the agent has been activated by or bound to the biological target.

After a peptide-detectable agent conjugate has been designed, synthesized, and optionally formulated, it can be tested in vitro by one skilled in the art to assess its biological and performance characteristics. For instance, different types of cells grown in culture can be used to assess the biological and performance characteristics of the agent. Cellular uptake, binding or cellular localization of the agent can be assessed using techniques known in the art, including, for example, fluorescent microscopy, fluorescence-activated cell sorting (FACS) analysis, immunohistochemistry, immunoprecipitation, in situ hybridization and Forster resonance energy transfer (FRET) or fluorescence resonance energy transfer.

By way of example, the peptide-detectable agent conjugate can be contacted with a sample for a period of time and then washed to remove any free agents. The sample can then be viewed using an appropriate detection device such as a fluorescent microscope equipped with appropriate filters matched to the optical properties of a fluorescent agent. Fluorescence microscopy of cells in culture or scintillation counting is also a convenient means for determining whether uptake and binding has occurred. Tissues, tissue sections and other types of samples such as cytospin samples can also be used in a similar manner to assess the biological and performance characteristics of the agents. Other detection methods including, but not limited to flow cytometry, immunoassays, hybridization assays, and microarray analysis can also be used.

In some embodiments, the peptide-detectable agent conjugates can be used in an in vitro assay for detecting agents that promote beta cell differentiation.

EXAMPLES

The invention is further described in the following examples, which do not limit the scope of the invention described in the claims.

Example 1. Preparation of Fluorescence-Labelled Exendin-4 Conjugates

Materials

All reagents were purchased from Sigma-Aldrich (St. Louis, Mo.) and used without further purification unless otherwise noted. Exendin-4 was obtained from Prospec (Rehovot, Israel) or as an injectable solution (250 μg/mL, Exenatide, Byetta; Amylin/Eli Lilly). Near-infrared fluorochrome Vivotag-680 (VT680-NHS ester) was purchased from VisEn (Bedford, Mass.) or from PerkinElmer (Waltham, Mass.).

Mass Spectrometry

Liquid chromatography electrospray ionization mass spectrometry (LC-ESI-MS) analysis and HPLC-purifications were performed on a Waters (Milford, Mass.) LC-MS system. For LC-ESI-MS analyses, a Waters XTERRA® C18 5 μm column was used. For preparative runs, an ATLANTIS® Prep T3 OBD™ 5 μM column was used. MALDI-MS spectra were collected on a VOYAGER-DE™ BIOSPECTROMETRY™ Workstation spectrometer (APPLIED BIOSYSTEMS™, Foster City, Calif.).

Three peptide-detectable agent conjugates were prepared using the following methods.

Preparation of Fluorescence-Labelled Exendin-4 Conjugates

1. Preparation of Exendin-4$_{K12}$-VT680

To a solution of 250 μg (0.06 μmol) of Exendin-4$_{K12}$ in 3.6 mL of a 25 mM Tris-buffered aqueous solution (pH=7.2), 1 mg VivoTag 680 (0.8 μmol) was added and the reaction mixture stirred at room temperature in the dark for 3 hours. The mixture was subjected to HPLC-purification, yielding the title compound as a blue solid (100 μg, 0.02 μmol, 33%). ESI-LC-MS m/z (%)=1769 [M−3H$^+$]$^{3-}$ (100).

2. Preparation of Exendin-4$_{40}$-VT680

Preparation of 11-Azido-3,6,9-Trioxaundecan-1-Amide-VT680

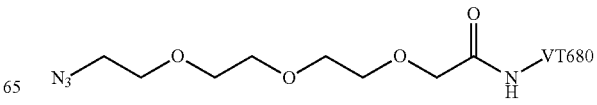

11-Azido-3,6,9-trioxaundecan-1-amide-VT680

To a solution of 10 mg (46 μmol) 11-Azido-3,6,9-trioxaundecan-1-amine in 300 μL 10×PBS, 2.5 mg (2 μmol) VivoTag 680 was added and the reaction solution stirred at room temperature in the dark for 2 hours. The crude mixture was directly subjected to HPLC-purification, yielding 1.5 mg (1.1 μmol, 56%) of the title compound as a blue solid. ESI-LC-MS m/z (%)=1342 $[M+H^+]^+$.

Preparation of Exendin-4$_{K12}$-VT-680

To a solution of 0.8 mg (0.2 μmol) Exendin-4(40-Pra) (Exendin-4 with the unnatural amino acid (S)-2-amino-4-pentynoic acid attached to the C-terminal end of Exendin-4) in 400 μL of a 25 mM Tris-buffered aqueous solution (pH=7.2), 50 μL of a 50 mM solution of L-ascorbic acid in $H_2O$ and 50 μL of a 50 mM aqueous $CuSO_4$ solution in $H_2O$ was added. 0.4 mg (0.3 μmol) of 11-Azido-3,6,9-trioxaundecan-1-amide-VT680 in 500 uL 2×PBS solution was then added and the reaction mixture was gently stirred at room temperature in the dark overnight. The crude mixture was diluted with 2 mL of 1×PBS and purified using an AMICON® Ultra 3 kDa (Millipore, Carrigtwohill, Ireland) centrifugal filter, before it was subjected to HPLC purification, yielding 0.3 mg (0.05 μmol, 25%) of the title compound as a blue film. ESI-LC-MS m/z (%)=1405 $[M-4H^+]^{4-}$ (100); 1873 $[M-3H^+]^{3-}$ (14).

3. Preparation of Exendin-4$_{X12}$-VT750

Preparation of 11-Azido-3,6,9-trioxaundecan-1-amide-VT750

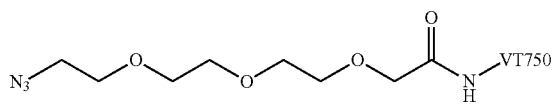

11-Azido-3,6,9-trioxaundecan-1-amide-VT750

To a solution of 10 mg (46 μmol) 11-Azido-3,6,9-trioxaundecan-1-amine in dichloromethane (DCM; 1 mL), 10 mg (8.5 μmol) VivoTag-S 750 and 20 μL triethylamine were added. The reaction solution was stirred at room temperature in the dark for 3 hours. Volatiles were removed under reduced pressure and the crude mixture was subsequently subjected to HPLC-purification, yielding 3.4 mg (3.1 μmol, 36%) of the title compound as a blue solid. ESI-LC-MS(+) m/z (%)=543.0 $[M+2H^+]^{2+}$ (100), 1084.5 $[M+H^+]^+$ (30); ESI-LC-MS(-) m/z (%)=541.0 $[M-2H^+]^{2-}$ (100), 1082.5 $[M-H^+]^-$ (20).

Preparation of Exendin-4$_{X12}$-VT750

To a solution of 3.4 mg (0.8 μmol) Exendin-4$_{X12}$ (X corresponding to the unnatural amino acid (S)-2-amino-4-pentynoic acid) in 400 μL of a 25 mM Tris-buffered aqueous solution (pH=7.2), 50 μL of a 50 mM solution of L-ascorbic acid in $H_2O$ and 50 μL of a 50 mM aqueous $CuSO_4$ solution in $H_2O$ were added. Subsequently, 1.2 mg (1.2 μmol) of 11-Azido-3,6,9-trioxaundecan-1-amide-VT750 in 500 μL 2× phosphate buffered saline (PBS) solution was added, and the reaction mixture was gently stirred at room temperature in the dark overnight. The crude mixture was then diluted with 2 mL of 1×PBS and purified using an AMICON® Ultra 3 kDa (Millipore, Carrigtwohill, Ireland) centrifugal filter, before being subjected to HPLC purification, yielding 2.7 mg (0.52 μmol, 64%) of the title compound as a blue film. ESI-LC-MS(+) m/z (%)=1310.2 $[M+4H^+]^{4+}$ (50), 1747.1 $[M+3H^+]^{3+}$ (100); ESI-LC-MS(-) m/z (%)=1745.2 $[M-3H^+]^{3-}$ (100).

Example 2. Characterization of Fluorescence-Labelled Exendin-4 Conjugates

MALDI-MS Spectra

To a suspension of sinapinic acid (5 μL, 10 mg/mL, $AcN/H_2O=1/1$, 0.5% TFA), 5 μL of fluorescence-labelled exendin-4 conjugate sample (approx. 100 μM in $H_2O$) was added and the carefully mixed solution purified via ZipTips (Millipore, Billercia, Mass.) prior to measurement. Each sample was also run with adrenocorticotropic hormone fragment 18-39 (ACTH fragment 18-39) as a calibration standard.

Tryptic Digest

To a solution of E4$_{K12}$-Fluorescence labeled conjugate (10.5 μL, approx. 10 μg), 15 μL $NaHCO_3$ (50 mM) and 1.5 μL dithiothreitol (DTT; 100 mM) was added, and the mixture was incubated at 95° C. for 5 minutes. Subsequently, 3 μL of IAA (100 mM) was added and the sample was incubated at room temperature for 20 minutes, before 1 μL of activated trypsin (100 ng/μL, Pierce, Rockford, Ill.) was added. This was followed by an incubation at 37° C. for 3 hours. An additional 1 μL of activated trypsin (100 ng/μL) was then added and the sample was further incubated at 37° C. for 2 hours, before being purified using ZipTips (Millipore, Billerica, Mass.) and subjected to MALDI-MS analysis.

Characterization Results from Exendin-4$_{K12}$-VT680 Conjugate

Figure 2A:
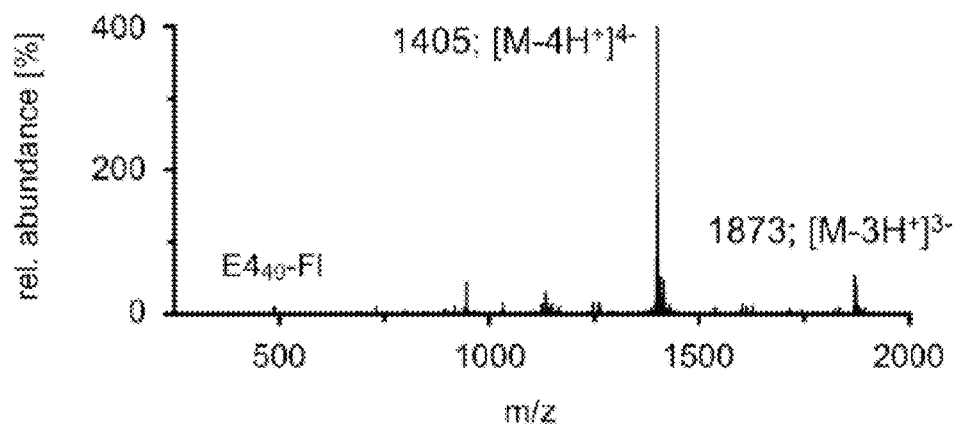
FIG. 2A is an image of an electrospray ionization mass spectrometry (ESI-MS) trace of Exendin-4 conjugated to the C-terminal of VT680 fluorophore.

Near infrared fluorescent Exendin-4 analogues were created via two different strategies (FIG. 1). In the first strategy, an alkyne-modified artificial amino acid (S)-2-amino-4-pentynoic acid was attached to the C-terminal end of exendin-4, yielding the peptide Exendin-4(40-Pra). To this peptide, an azide-modified near infrared (NIR) fluorochrome 11-azido-3,6,9-trioxaundecan-1-amide-VT680 was covalently attached using standard copper catalyzed click-chemistry protocols, yielding the Exendin-4-like NIR-fluorochrome, E4$_{40}$-VT680. 11-azido-3,6,9-trioxaundecan-1-amide-VT680 was generated in good yields (56%) by conjugation of 11-azido-3,6,9-trioxaundecan-1-amine to the commercially available NIR fluorochrome VT680-NHS ester in the presence of triethylamine. The structural identity of the exendin-like NIR-fluorochrome Exendin-4$_{40}$-VT680, was confirmed using liquid chromatography-mass spectrometry (LC/MS) (FIG. 2A) analysis, which confirmed the expected mass of 5623 g/mol (m/z (%)=1405 $[M-4H^+]^{4-}$ (100); 1873 $[M-3H^+]^{3-}$ (14)).

Figure 2B:
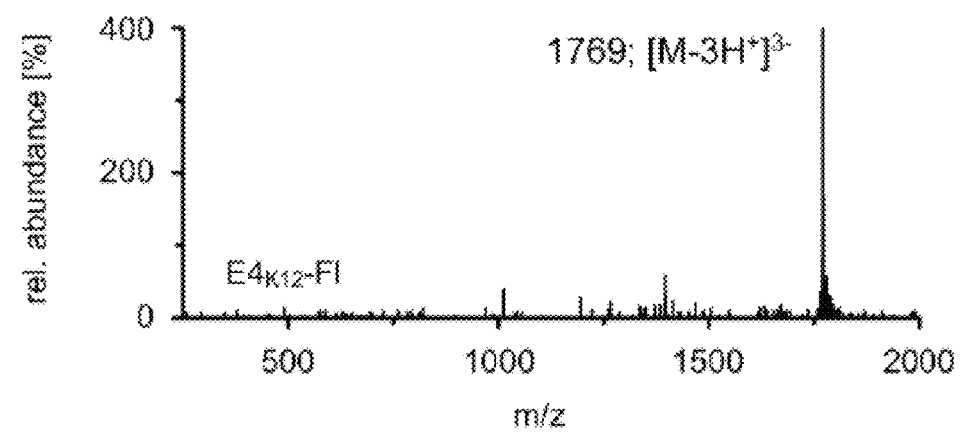
FIG. 2B is an image of ESI-MS trace of Exendin-$4_{K12}$ conjugated to VT680 fluorophore.

The second approach was based on the direct amide coupling reaction of VT680-NHS ester with the amino groups of Exendin-4, facilitated in a Tris-HCl buffered aqueous solution. Although Exendin-4 offers multiple nucleophilic amino sites, which can all theoretically react with NHS esters at one or multiple sites, only three reaction products were detected in the crude reaction mixture via LC/MS under current reaction conditions. All of the products had the same mass of 5311 g/mol (m/z (%)=1769 $[M-3H^+]^{3-}$ (100); FIG. 2B), which corresponded to the addition of a single fluorochrome per Exendin-4. Three products were observed in ratios of 5/5/90. The major product (90%) was isolated using preparative HPLC, yielding the Exendin-4-like NIR fluorochrome Exendin-4$_{K12}$-VT680 (FIG. 1).

Figure 2C:
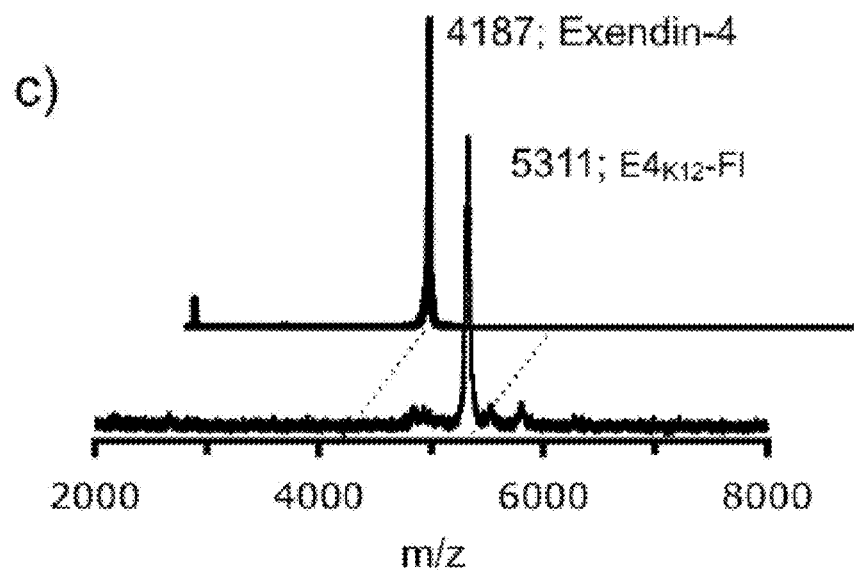
FIG. 2C is an image of a matrix assisted laser desorption ionization mass spectrometry (MALDI-MS) trace of Exendin-4 and Exendin-$4_{K12}$-VT680.
Figure 2D:
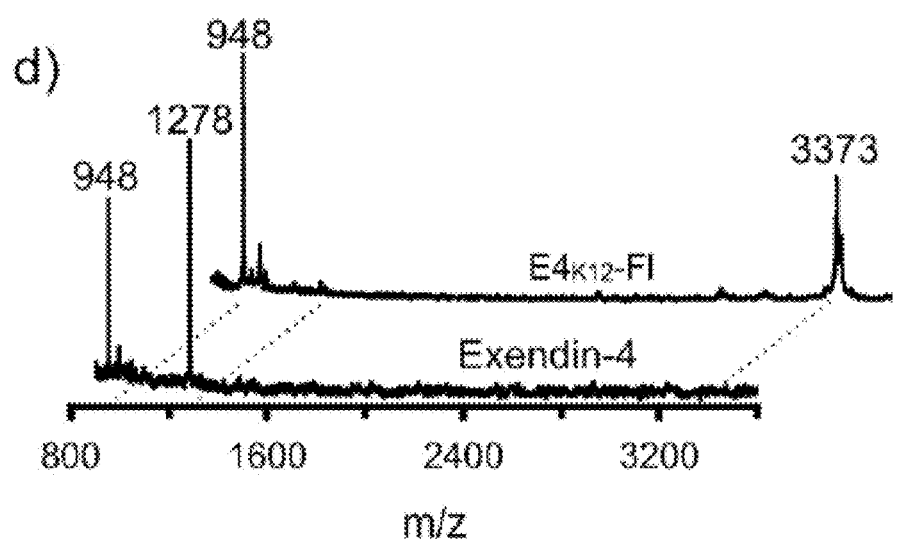
FIG. 2D is an image of a MALDI-MS trace of tryptic digest fragments of Exendin-4 and Exendin-$4_{K12}$-VT680.

The mass of Exendin-4$_{K12}$-VT680 was analyzed using matrix assisted laser desorption ionization mass spectrometry (MALDI-MS), which confirmed the exendin-4-like NIR fluorochrome to be composed of exendin-4 and a single fluorochrome molecule (m/z=5311, FIG. 2C). Structural analysis of the compound was determined by tryptic digestion of both Exendin-4$_{K12}$-VT680 and Exendin-4. Whereas Exendin-4 displayed two strongly ionizing fragments at 1278 Da (H1-K12) and 948 Da (L21-K27), tryptic digest of Exendin-4$_{K12}$-VT680 did not result in the formation of a 1278 Da fragment, but showed a dominant peak at 3373 Da (FIG. 2D). The fragment corresponded to amino acids H1-R20 (2251 Da) plus the mass of the fluorochrome (1123 Da). Observation of a peak at 3373 Da for Exendin-4$_{K12}$-VT680 but not for Exendin-4 indicated that the fluorochrome was part of that fragment and that it was conjugated to amino acid K12. If the fluorochrome were not conjugated to K12, the fragment would have been digested by trypsin at the K12-position into two smaller fragments. The predominant attachment of the fluorochrome to K12 compared to other nucleophilic residues (e.g. K27 or the N-terminus) is likely explained by either sterically or electronically favored conformations of K12.

Characterization Results from Exendin-4$_{K12}$-VT750 Conjugate

Figures 3A, 3B:
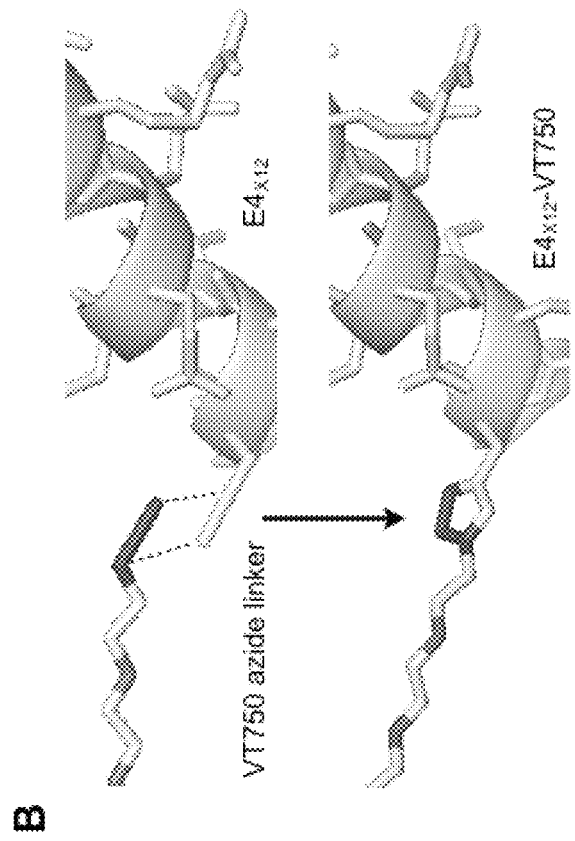
FIG. 3A is a table of the amino acid sequences and molecular weight of synthesized Exendin-4 in which the lysine at position 12 has been replaced with (S)-2-amino-4-pentynoic acid, and Exendin-4 in which the lysine at position 12 has been replaced with (S)-2-amino-4-pentynoic acid conjugated to a VT750 fluorophore.
FIG. 3B is a schematic model of the bioorthogonal copper-catalyzed click reaction between Exendin-4 where the lysine at position 12 has been replaced with (S)-2-amino-4-pentynoic acid and azide-functionalized VT750 fluorophore.
Figure 3C:
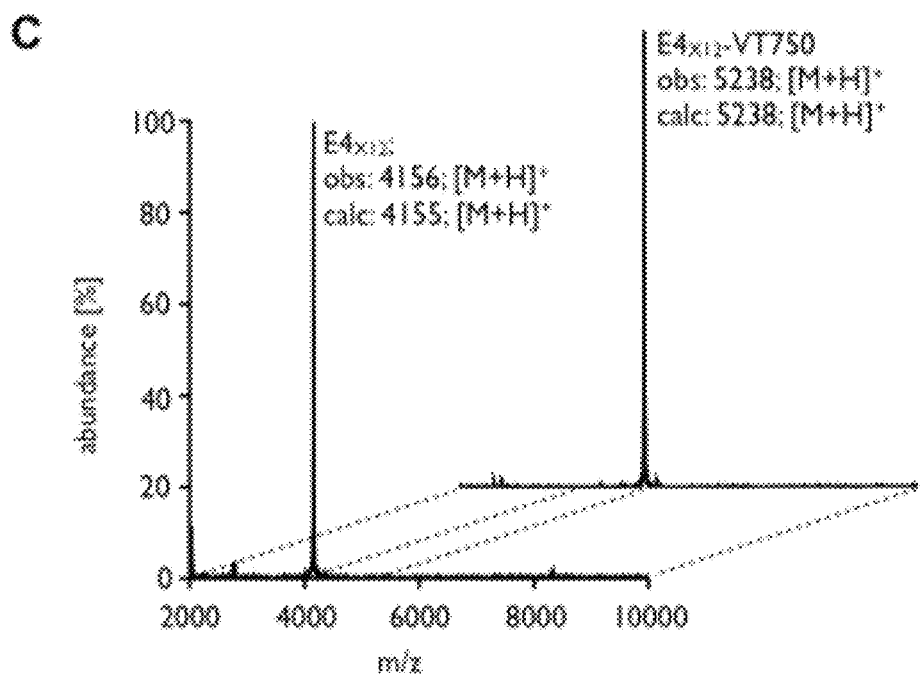
FIG. 3C is an image of a MALDI-MS trace of Exendin-$4_{X12}$ (where the lysine at position 12 has been replaced with (S)-2-amino-4-pentynoic acid) and Exendin-$4_{X12}$ conjugated to a VT-750 fluorophore.
Figure 3D:
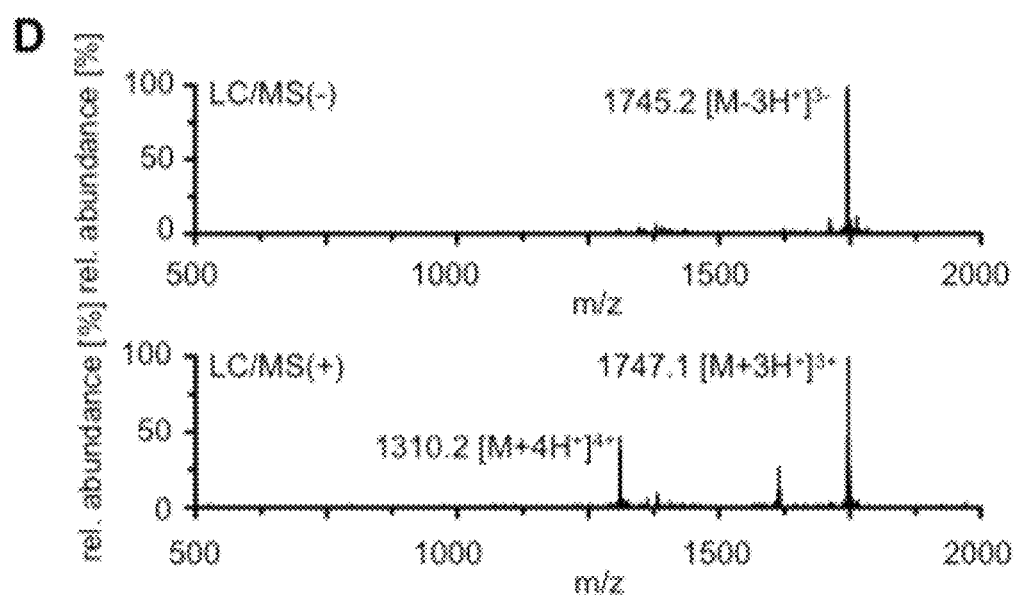
FIG. 3D is an image of the negative (top trace) and positive (bottom trace) polarized high performance liquid chromatography-electrospray ionization mass spectroscopy (HPLC-ESI MS) of Exendin-$4_{X12}$ conjugated to a VT750 fluorophore.
Figure 3E:
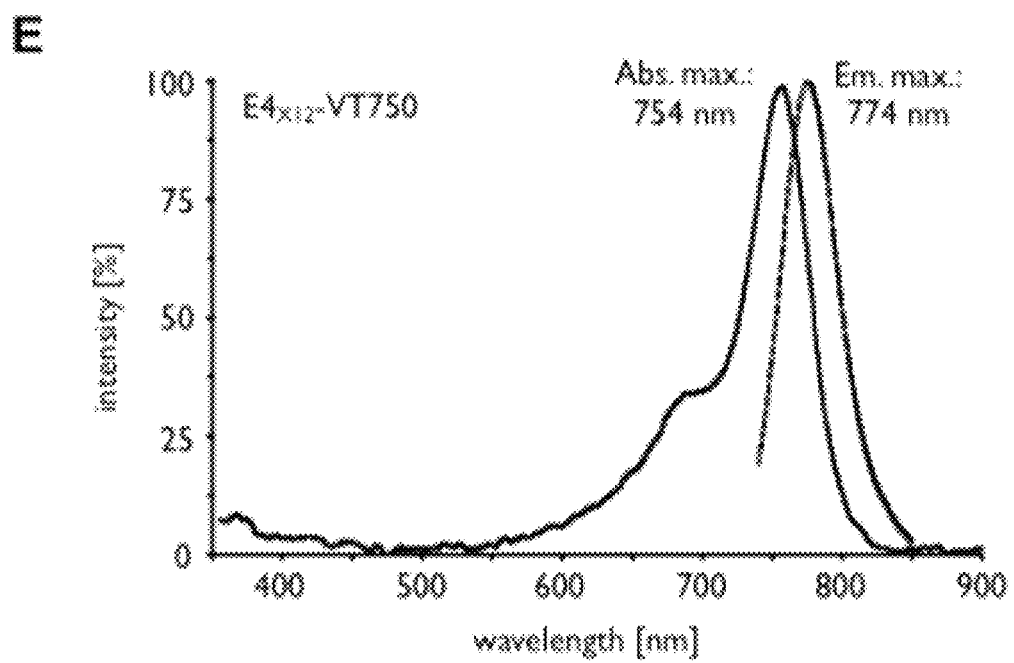
FIG. 3E is an image of an absorption and emission spectra of Exendin-$4_{X12}$ conjugated to a VT750 fluorophore.

The amino acid lysine at the 12 position (K12) of the exendin-4 sequence was used as a modification point without significant reduction of peptide/GLP-1R target binding. Based on earlier findings, this was in contradistinction to fluorochrome modification of a lysine group at the 40 position (K$_{40}$), which has been shown to affect target selectivity (Reiner T, et al. *Bioconjug Chem* 21:1362-1368, 2010), presumably due to the close proximity of this lysine group to the extracellular domain of the GLP-1R binding site. To facilitate site-specific K$_{12}$ labeling, a neopeptide, Exendin-4$_{X12}$ was designed, which allows attachment of desired markers via Copper(I)-catalyzed azide-alkyne cycloaddition reactions (CuAAC) (Rostovtsev et al. *Angew Chem Int Ed Engl* 41:2596-2599, 2002). Based on the Exendin-4 sequence, we replaced K$_{12}$ with the unnatural alkyne-amino acid (S)-2-amino-4-pentynoic acid. Simple CuAAC conditions (aqueous buffer, CuSO$_4$, L-ascorbic acid) allowed attachment of the azide-functionalized NIR-fluorophore (VT750) to Exendin-4$_{X12}$ (FIGS. 3A and 3B). This produced the NIR GLP-1R probe with an overall synthetic yield of 64% from starting materials. HPLC-ESI/MS and MALDI-MS spectrometry confirmed the identity of Exendin-4$_{X12}$-VT750, and gave mass-to-charge ratios (m/z) corresponding to the calculated masses (FIGS. 3C and 3D). The maximum absorbance/emission peaks for Exendin-4$_{X12}$-VT750 were 754 nm and 774 nm, respectively (FIG. 3E).

Example 3. Ex Vivo Determination of Exendin-4$_{K12}$-VT680 Accumulation in GLP-1R Expressing Cells Cell Culture Mouse insulinoma-derived MIN6 cells were used between passages 26 and 40 and grown in high-glucose Dulbecco's Modified Eagles Medium (DMEM) containing 15% (v/v) heat-inactivated fetal bovine serum (FBS), 50 U/ml penicillin, and 10 µg/ml streptomycin. Human embryonic kidney cells (HEK 293 cells), stably expressing human GLP-1R (HEK/hGLP-1R), were grown in high glucose DMEM containing 10% (v/v) heat-inactivated FBS, 50 U/ml penicillin, 10 µg/ml streptomycin, 1 mM sodium pyruvate, and 150 µg/ml G418. GLP-1R negative NIH-3T3 fibroblasts (ATCC) were grown in high glucose DMEM containing 10% (v/v) heat-inactivated FBS, 50 U/ml penicillin, and 10 µg/ml streptomycin.

Western Blot

MIN6, HEK/hGLP-1R or NIH-3T3 cells, seeded into 6-well plates were washed twice with ice-cold PBS and lysed on ice with 200 µl ice-cold RIPA lysis buffer. Protein concentrations were determined using bicinchoninic acid (BCA) protein assays (Pierce, Rockford, Ill.). Cell lysates (50 µg) were subjected to SDS-PAGE, followed by immunoblotting using a specific anti-GLP-1R antibody (Abcam), and detection with chemiluminescence (Pierce, Rockford, Ill.).

Cellular Imaging

MIN6 (2×10$^5$ cells/well), HEK/hGLP-1R (7.5×10$^4$ cells/well) or NIH-3T3 (7.5×10$^4$ cells/well) cells were seeded into 8-well chamber slides (LabTek, Rochester, N.Y.) and incubated for 48 hours before incubation with 100 nM of E4$_{K12}$-Fl for the indicated time points at 37° C. Cells were washed three times with PBS before subjected to imaging. MIN6, HEK/hGLP-1R and NIH 3T3 cells were imaged on an Olympus FluoView1000 confocal laser scanning microscope with an Olympus XLPan N 25× (N.A. 1.1) water immersion objective and the FluoView 1000 Vers. 2.1a program. Exendin-4$_{K12}$-VT680 was imaged using a 635 nm laser, dichroic mirrors DM405/488/559/635 and SDM640 and a barrier filter BA655-755.

Dose-Response Assays

MIN6 (1×10$^5$ cells/well), HEK/hGLP-1R (3×10$^4$ cells/well) or NIH-3T3 (3×10$^4$ cells/well) cells were seeded into 96-well plates and incubated for 48 hours before adding different concentrations of Exendin4$_{K12}$-VT680. After incubating for 1 hour at 37° C., cells were washed three times with PBS and the fluorescence levels were measured with a SynergyMx plate reader (Biotek) with excitation at 620 nm and emission at 690 nm. Following fluorescence measurement, proteins were extracted using RIPA lysis buffers and quantified using BCA (Pierce, Rockford, Ill.).

Blocking Experiments

MIN6 (1×10$^5$ cells/well), HEK/hGLP-1R (3×10$^4$ cells/well) or NIH-3T3 (3×10$^4$ cells/well) cells were seeded into 96-well plates and incubated for 48 hours before incubation with either Exendin-4 (100 nM) for 1 hour at 37° C. and subsequently Exendin-4$_{K12}$-VT680 (10 nM) for 1 hour at 37° C., or just Exendin-4$_{K12}$-VT680 (10 nM) for 1 hour at 37° C. Following the incubation, cells were washed three times with PBS and the fluorescence levels were measured with SynergyMx plate reader (Biotek) with excitation at 620 nm and emission at 690 nm. Following fluorescence measurement, proteins were extracted using RIPA lysis buffers (24) and quantified using BCA (Pierce, Rockford, Ill.).

Results

Figure 4A:
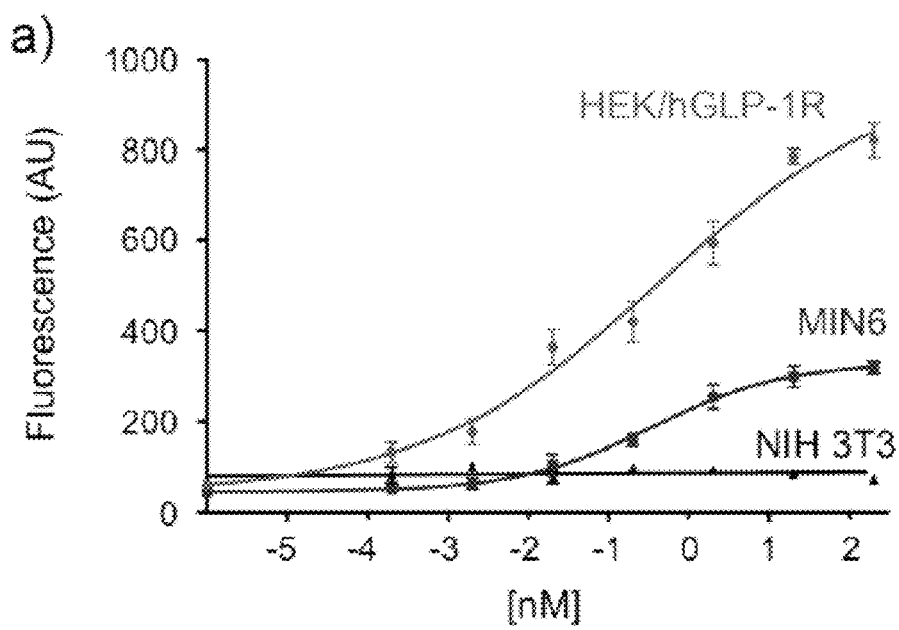
FIG. 4A is a line graph of dose-response curves of Exendin-$4_{K12}$ conjugated to a VT680 fluorophore where GLP-1R is either overexpressed (HEK/hGLP-1R) or naturally expressed (MIN6), and of a GLP-1R negative (NIH 3T3) cell line.
Figure 4B:
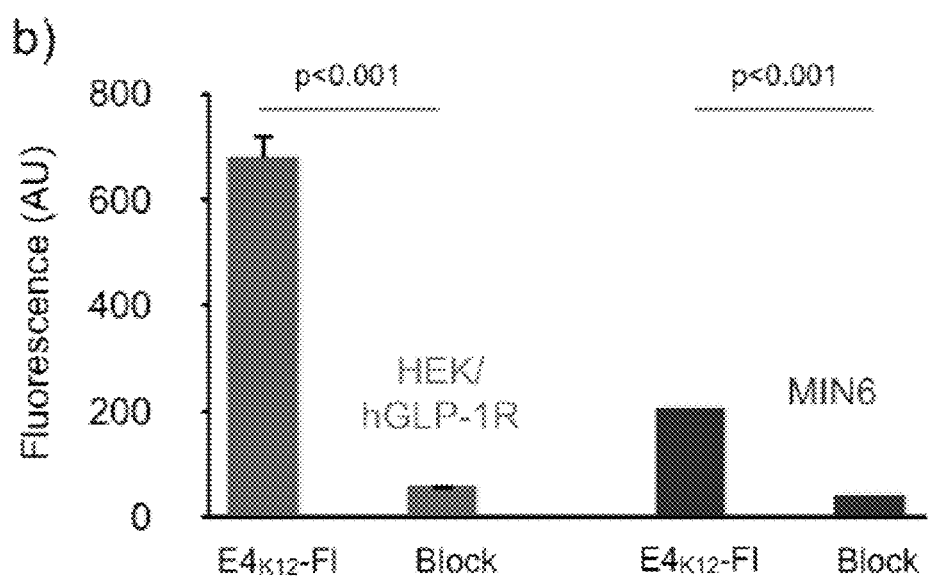
FIG. 4B is a bar graph of the blocking of Exendin-$4_{K12}$ conjugated to VT680 (10 nM) with Exendin-4 (100 nM).
Figure 4C:
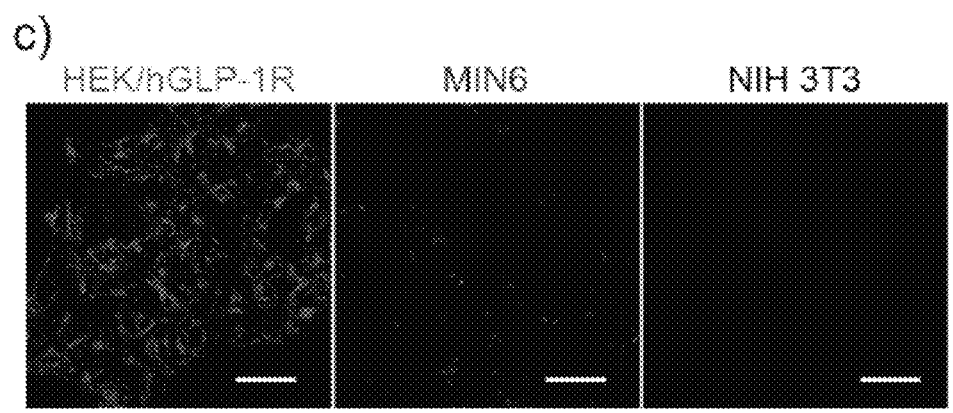
FIG. 4C is an image of live cell microscopy. The cell lines HEK/hGLP-1R, MIN6 or NIH 3T3 were treated with Exendin-4$_{K12}$ conjugated to VT680 (10 nM) and then imaged (Scale bar: 50 μm).
Figure 4D:
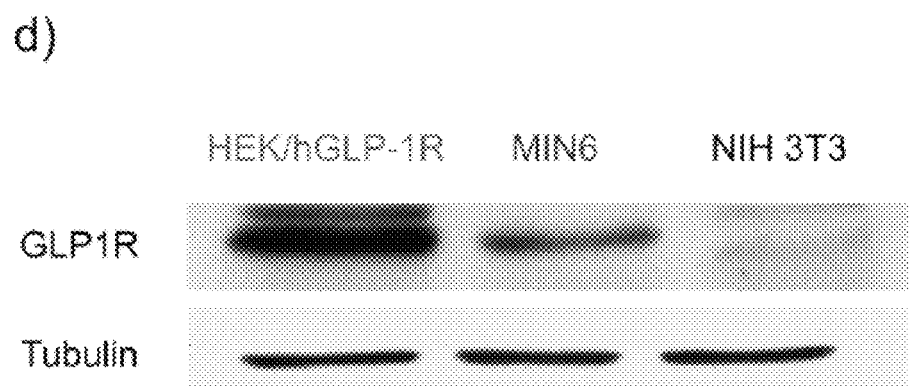
FIG. 4D is an image of a Western Blot of HEK/hGLP-1R, MIN6 and NIH 3T3 cell lines against GLP-1R and tubulin.

In order to determine accumulation of Exendin-4$_{K12}$-VT680 on GLP-1R expressing cells, the compounds were tested against human GLP1-R overexpressing HEK/hGLP-1R cells (HEK/hGLP-1R), GLP-1R naturally expressing MIN6, and against GLP-1R negative NIH 3T3 cells (FIGS. 4A-4D). The expression levels of GLP-1R were then analyzed by staining the respective cell lysates with an anti-GLP-1R antibody and equal cell lysate concentrations were analyzed by staining against tubulin in western blots (FIGS. 4A-4D). Western blotting confirmed GLP-1R to be absent in NIH 3T3 cells and overexpressed in transformed HEK/hGLP-1R cells. Each cell line was incubated with different concentrations of Exendin-4$_{K12}$-VT680 for 1 hour. The cells were later washed and their fluorescence measured. The fluorescent signal was normalized to the number of cells present in each well. GLP-1R overexpressing HEK/hGLP-1R cells displayed the highest fluorescence, followed by insulinoma-derived MIN6 cells. GLP-1R negative NIH 3T3 cells did not show any discernible fluorescence (FIG. 4A). For HEK/hGLP-1R cells, a binding $EC_{50}$ of 0.3±0.2 nM was determined and for MIN6 cells, the observed $EC_{50}$ was 0.5±0.3 nM. These findings were corroborated using confocal microscopy (FIG. 4C). Blocking experiments with non-fluorescent Exendin-4 were subsequently conducted. Pre-treated HEK/hGLP-1R cells were observed to have a 12-fold lower fluorescence and pre-treated MIN6 cells a 5-fold lower fluorescence. Finally, we also tested the terminally labeled Exendin-$4_{40}$-VT680, which did not show strong preferential accumulation in GLP-1R expressing cell lines.

Example 4. Ex Vivo Determination of Exendin-$4_{K12}$-VT750 Accumulation in GLP-1R Expressing Cells Cell Culture Mouse insulinoma-derived MIN6 cells were used between passages 26 and 40, and were grown in high-glucose Dulbecco's Modified Eagle's Medium (DMEM) containing 15% (v/v) heat-inactivated fetal bovine serum (FBS), 50 U/mL penicillin, and 10 µg/mL streptomycin. Human embryonic kidney cells, stably expressing human GLP-1R (HEK/hGLP-1R) were grown in high-glucose DMEM containing 10% (v/v) heat-inactivated FBS, 50 U/mL penicillin, 10 µg/mL streptomycin, 1 mM sodium pyruvate, and 150 µg/mL of the antibiotic G418. GLP-1R negative NIH-3T3 fibroblasts (ATCC) were grown in high-glucose DMEM containing 10% (v/v) heat-inactivated FBS, 50 U/mL penicillin, and 10 µg/mL streptomycin.

Cell-Labeling Assays

MIN6 ($1 \times 10^5$ cells/well), HEK/hGLP-1R ($3 \times 10^4$ cells/well) or NIH-3T3 ($3 \times 10^4$ cells/well) cells were seeded into 96-well plates and incubated for 48 hours, before incubation with various concentrations of Exendin-$4_{x12}$-VT750 for 90 minutes at 37° C. Following incubation, cells were washed once with PBS and the fluorescence levels were measured with a SynergyMx (Biotek, Winooski, Vt.) plate reader at an excitation of 755 nm and emission of 775 nm. After measurement of fluorescence, proteins were extracted using radioimmunoprecipitation assay (RIPA) lysis buffers and protein levels were determined using a bicinchoninic acid (BCA) assay (Thermo Fisher Scientific, Waltham, Mass.).

Blocking Experiments

MIN6 ($1 \times 10^5$ cells/well) or HEK/hGLP-1R ($3 \times 10^4$ cells/well) cells were seeded into 96-well plates and were cultured for 48 hours. The cells were then either incubated with Exendin-$4_{x12}$-VT750 (10 nM) for 90 minutes at 37° C. alone, or with increasing doses of exendin-4 (0 nM-500 nM) for 1 hour at 37° C. and subsequently with Exendin-$4_{x12}$-VT750 (10 nM) for 90 minutes at 37° C. Following incubations, cells were imaged and proteins quantified as described above.

Cell Imaging

MIN6 ($2 \times 10^5$ cells/well), HEK/hGLP-1R ($7.5 \times 10^4$ cells/well) or NIH-3T3 ($7.5 \times 10^4$ cells/well) cells were seeded onto 8-well chamber slides (LabTek, Rochester, N.Y.) and cultured for 48 hours (at 37° C.). The cells were then either incubated with 10 nM of Exendin-$4_{x12}$-VT750 (90 min, 37° C.) alone, or underwent an initial incubation with 3.5 µM exendin-4 (30 minutes, 37° C., and washed 1× with growth medium) before subsequent incubation with 10 nM E$4_{x12}$-VT750 (90 min, 37° C.). The cells were then washed once with growth medium and once with 1×PBS. MIN6, HEK/hGLP-1R and NIH 3T3 cells were imaged using an intravital laser scanning microscope (IV100, Olympus Corporation, Tokyo, Japan).

Binding, Affinity and Inhibition Results

Figure 5A:
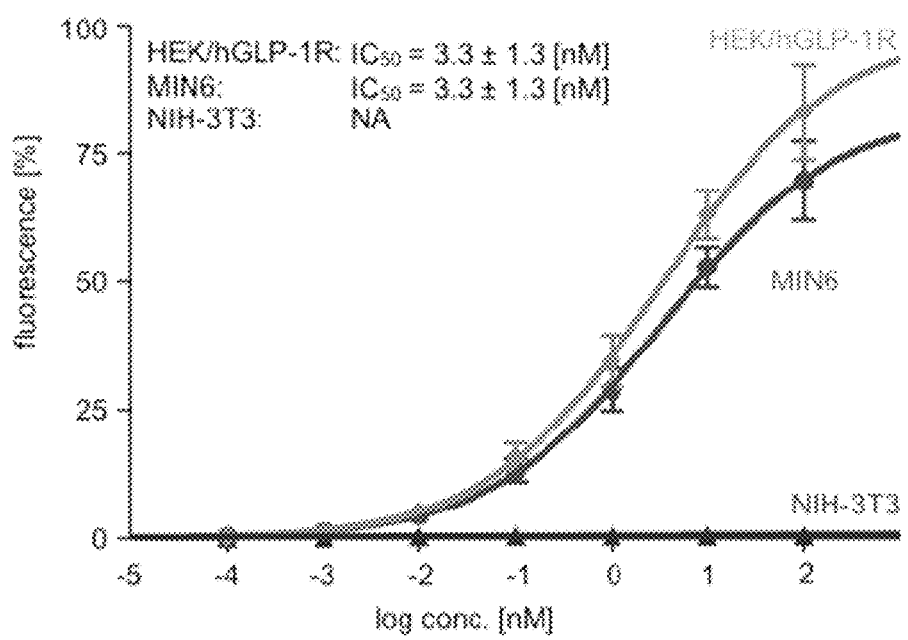
FIG. 5A is a line graph of cell binding assays of different concentrations of Exendin-4$_{X12}$ conjugated to VT750 against HEK/hGLP-1R (GLP-1R overexpressing), MIN6 (naturally expressing GLP-1R) and NIH 3T3 (GLP-1R negative).
Figure 5B:
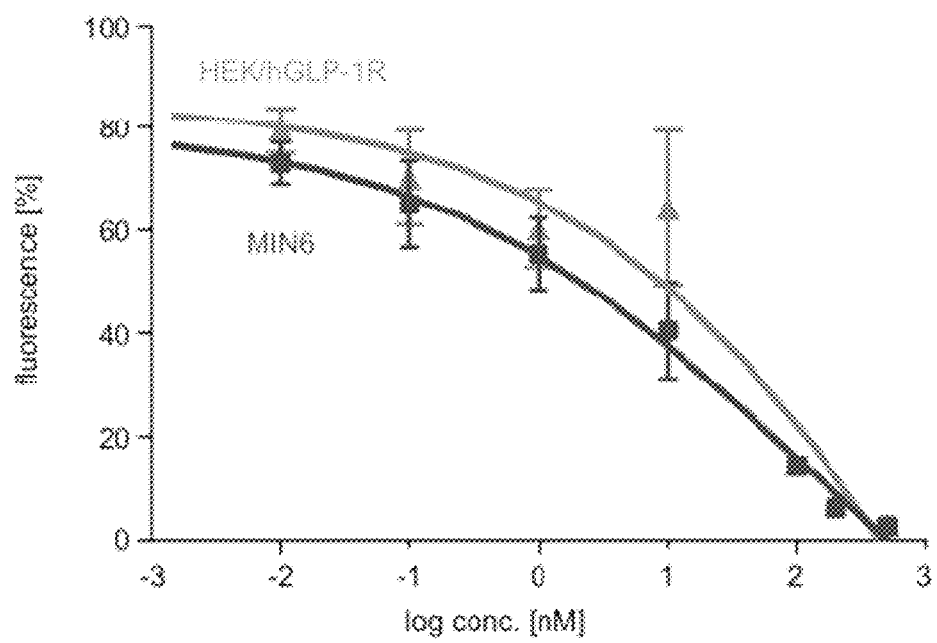
FIG. 5B is a line graph of in vitro blocking experiments of Exendin-4$_{X12}$ conjugated to VT750/GLP-1R binding (E4$_{X12}$-VT750=10 nM) with different concentrations of Exendin-4.

Cell assays were performed using the MIN6 cell line, which naturally expresses GLP-1R, HEK/hGLP-1R cells which ectopically express GLP-1R, and GLP-1R-negative NIH 3T3 cells. Incubation of each line with different concentrations of Exendin-$4_{x12}$-VT750 revealed increasing fluorescence for MIN6 and HEK/hGLP-1R cells, whereas no increase in fluorescence was detectable for NIH 3T3 cells (FIG. 5A). The $IC_{50}$-values for both MIN6 and HEK/hGLP-1R cells were 3.3±1.3 nM. In order to probe the selectivity of Exendin-$4_{x12}$-VT750 for GLP-1R, both MIN6 and HEK/hGLP-1R cells were first incubated with different concentrations of Exendin-4 (0 nM to 500 nM) and a fixed concentration of Exendin-$4_{x12}$-VT750 (10 nM, FIG. 5B). Upon pre-incubation with exendin-4, a concentration dependent decrease in E$4_{x12}$-VT750 fluorescence signal was observed. Indeed, pre-incubation with 500 nM Exendin-4 (a 50-fold excess of Exendin-4 relative to Exendin-$4_{x12}$-VT750) produced a near-quantitative reduction in fluorescence signal. These results not only show that Exendin-$4_{x12}$-VT750 was selectively taken up by GLP-1R-expressing cell lines, but also that its uptake could be selectively inhibited upon addition of the unlabeled analogue.

Figure 5C:
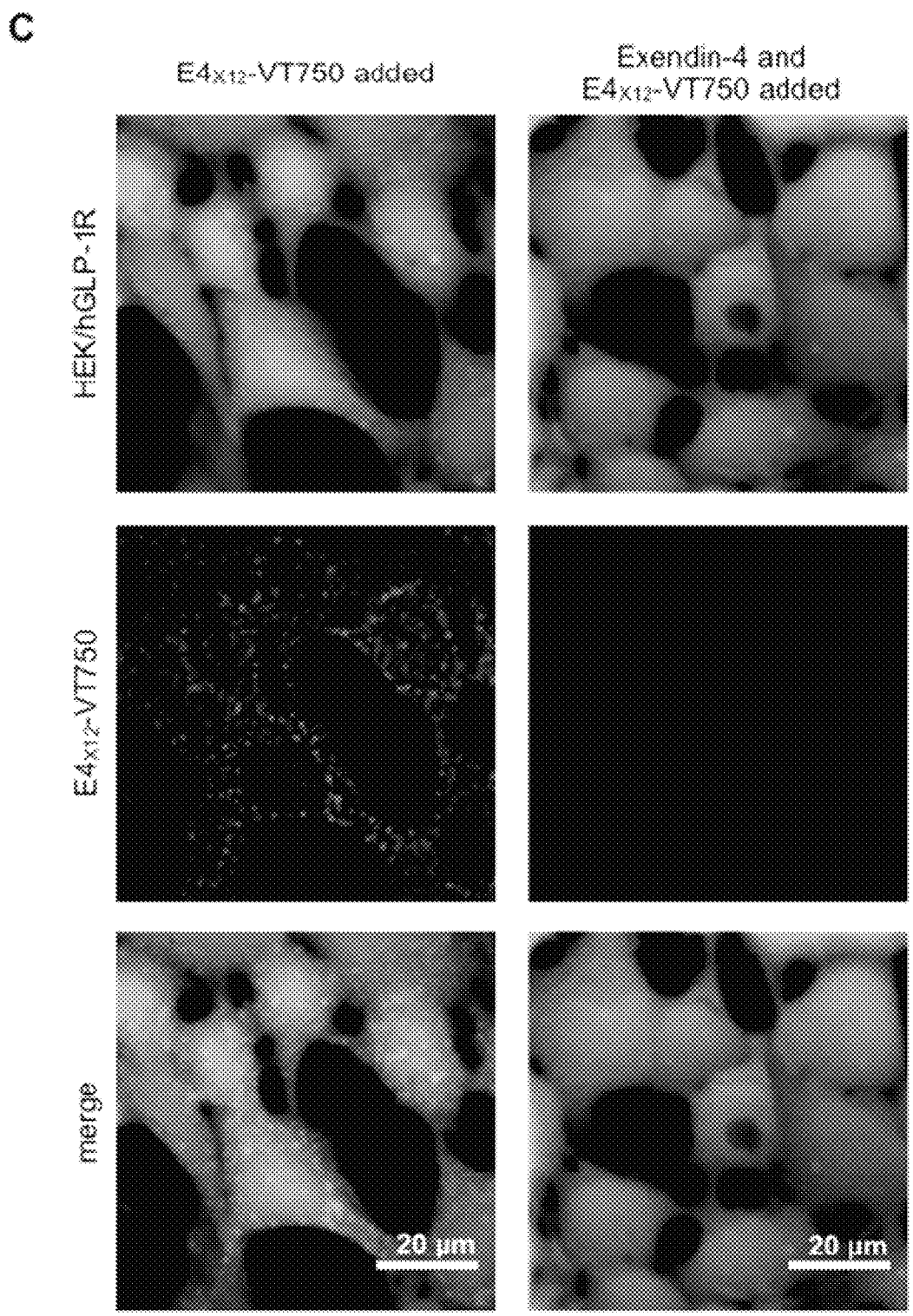
FIG. 5C is fluorescence image of cells following incubation with Exendin-4$_{X12}$ conjugated to VT750 alone (left column), or after pre-incubation with excess Exendin-4 (right column) (Scale bar: 20 μm).

Binding of GLP-1 to GLP-1R resulted in internalization of the peptide into cells and its localization in endosomal compartments. In order to visualize the cellular localization of Exendin-$4_{x12}$-VT750, HEK/hGLP-1R (FIG. 5C) and MIN6 cells (data not shown) were incubated with a 10 nM solution of Exendin-$4_{x12}$-VT750 for 90 minutes. Cells were stained with CellTracker Green to visualize the cell boundaries. The fluorescent probe Exendin-$4_{x12}$-VT750, like GLP-1, could be identified inside beta cells in vesicular compartments (FIG. 5C, left column). In contrast, similar to what was seen with competitive binding assays (FIG. 5B), pre-incubation with unlabeled Exendin-4 suppressed the Exendin-$4_{x12}$-VT750 fluorescence signal (FIG. 5C, right column).

Example 5. In Vivo Quantification of Beta Cell Mass Using Exendin-$4_{x12}$-VT680

Animals

NOD MIP-GFP mice (NOD.Cg-Tg(Ins-EGFP)Hara/QtngJ), that express the fluorescent protein EGFP within the islets under the mouse insulin 1 promoter were obtained from The Jackson Laboratory (Bar Harbor, Me.). All procedures and animal protocols were approved by the subcommittee on Research Animal care at Massachusetts General Hospital.

Animal Preparation

Nondiabetic male NOD MIP-GFP mice were anesthetized with 2% isoflurane and 2 L/minute $O_2$. The peritoneal cavity was opened with a transverse incision in the disinfected abdominal wall. The gastric-splenic ligament was dissected and the pancreas carefully exteriorized. Robust blood flow was observed in the pancreatic arteries for the duration of each experiment and pancreas perfusion was confirmed by observation of a circulating fluorescent vascular agent (Angiosense 750, VisEn, Bedford, Mass.). The exteriorized pancreas was completely submerged in temperature-controlled lactated Ringer's solution. The temperature near the spleen was carefully monitored using an Omega HH12A thermometer with fine wire thermocouples (Omega Engineering Inc., Stamford, Conn.) and kept at 37° C. A tail vein catheter, made using a 30 G×½" needle inserted into CLAY ADAMS® Polyethylene10 tubing, was inserted prior to surgery. Subsequently, 200 µL (4 nmol/200 µL) of Exendin-$4_{K12}$-VT-680 and 10 minutes after the initial injection, another 200 µL (4 nmol/200 µL) of Exendin-$4_{K12}$-VT680 was injected via the tail vein catheter.

Intravital Laser Scanning Microscopy

Images were collected with a prototypical intravital laser scanning microscope (IV100, Olympus Corporation, Tokyo, Japan) (26) using an Olympus 4× (UplanSApo N.A. 0.16), and 20× (UplanFL N.A. 0.5) objective and the Olympus FluoView FV300 version 4.3 program. Samples were excited at 488 nm with an air-cooled argon laser (Melles Griot, Carlsbad, Calif.) for visualization of the GFP expressing islet-cells, at 633 nm with a HeNe—R laser (Model 05LHP925, Melles Griot) for visualization of Exendin-$4_{K12}$-VT680, and at 748 nm with a red diode laser (Model FV10-LD748, Olympus Corporation, Tokyo, Japan) for visualization of the blood pool agent (AngioSense-780, VisEn Medical, MA). Light was collected using custom-built dichroic mirrors SDM-560, SDM640, and SDM-750, and with emission filters BA 505-550, BA660-730, and BA 770 nm IF (Olympus Corporation, Tokyo, Japan). The Exendin-$4_{K12}$-VT680 signal was collected sequentially to the other channels to avoid bleed-through into the VT680 channel. A prototypical tissue stabilizer (Olympus Corporation, Tokyo, Japan) was used to reduce motion and to stabilize the focal plane. The stabilizer was attached to the objective and its z-position was finely adjusted using a micrometer screw to apply soft pressure on the tissue.

Histology

Nondiabetic male NOD MIP-GFP mice were cannulated with a tail vein catheter, made using a 30 G×½" needle inserted into CLAY ADAMS® Polyethylene10 tubing. Subsequently, 200 µL (4 nmol/200 µL) of Exendin-$4_{K12}$-VT680 was injected via the tail vein catheter. Mice were sacrificed 2 hours after the initial injection, the pancreas was harvested and frozen in OCT compound (Sakura, Finetek, Torrance, Calif.) with isopentane on dry ice. The frozen tissues were sectioned (thickness: 6 µm) and mounted on microscope slides. Without further processing, tissue samples were excited with an EXFO X-Cite™ 120 light source (EXFO Photonic Solutions Inc. Ontario, Canada) and imaged with a Nikon Eclipse 80i microscope with either a 10× Plan Fluor N.A. 0.3 and a 20× Plan Apo 0.75 objective (Nikon corporation, USA) respectively. GFP fluorescence was observed with a Chroma HQ FITC filter cube (HQ480/40×EX, dichroic Q505LP BS, and emission filter HQ535/50m EM) and Exendin-VT680 fluorescence with a Chroma Cy5.5 filter cube (HQ650/45×EX, dichroic Q680LP BS, and emission filter HQ710/50m EM; Chroma Technology Corp., VT, USA). Images were captured with a Cascade Model 512B camera (Roper Scientific, Tucson, Ariz.). Validation of fluorescence signals employed immunohistochemistry for insulin (Insulin (H-86), Santa Cruz Biotechnology, Santa Cruz, Calif.) using the avidin-biotin peroxidase method. The reaction was visualized with a 3-amino-9-ethyl-carbazole substrate (AEC, Sigma Chemical, Saint Louis, Mo.). Adjacent sections treated with nonimmune IgG provided controls for antibody specificity.

Results

Figure 6:
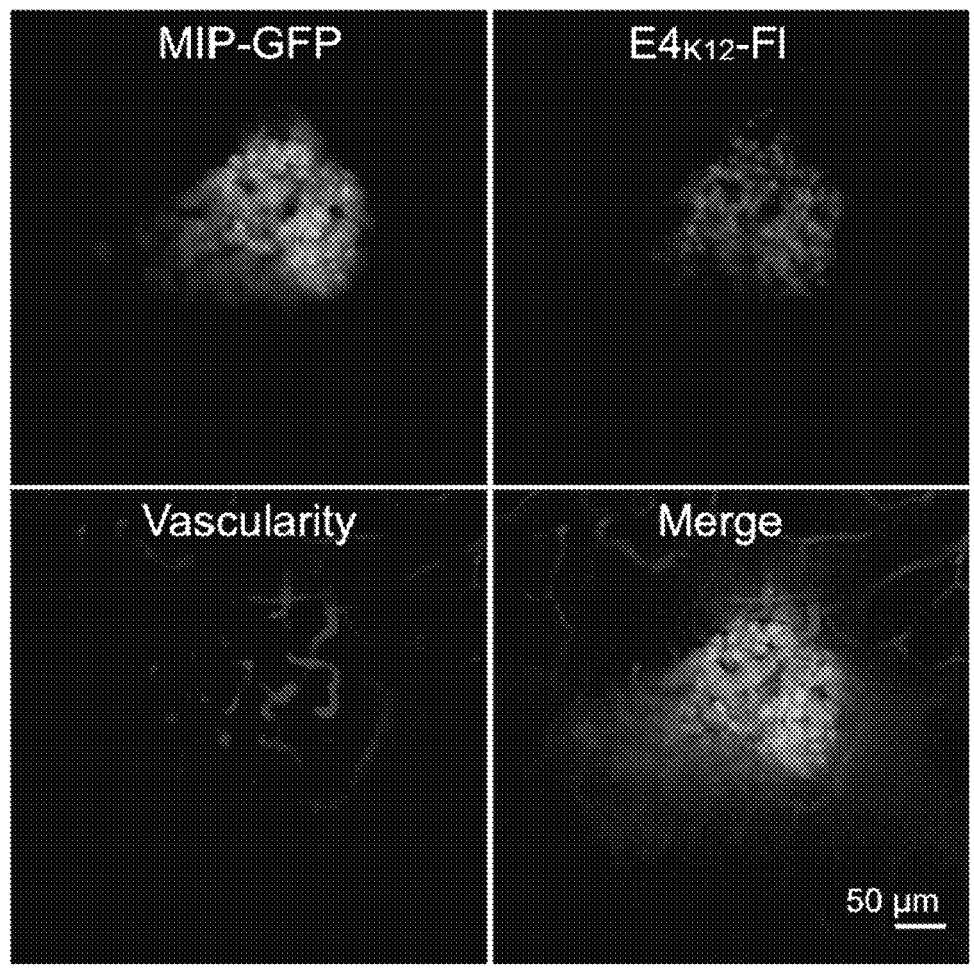
FIG. 6 is an in vivo image of Exendin-4$_{K12}$ conjugated to VT680 in a pancreatic islet of a live NOD MIP-GFP mouse; GFP-expressing pancreatic beta cells are depicted in the top left image; Exendin-4$_{K12}$ conjugated to VT680 accumulation (dose: 0.4 nmol/g) is depicted in the top right image; fluorescent vascular agent is depicted in the bottom left image; and merging of these three images is depicted in the bottom right. All images acquired with 20× objective in anesthetized live mice (Scale bar: 50 μm).
Figure 7:
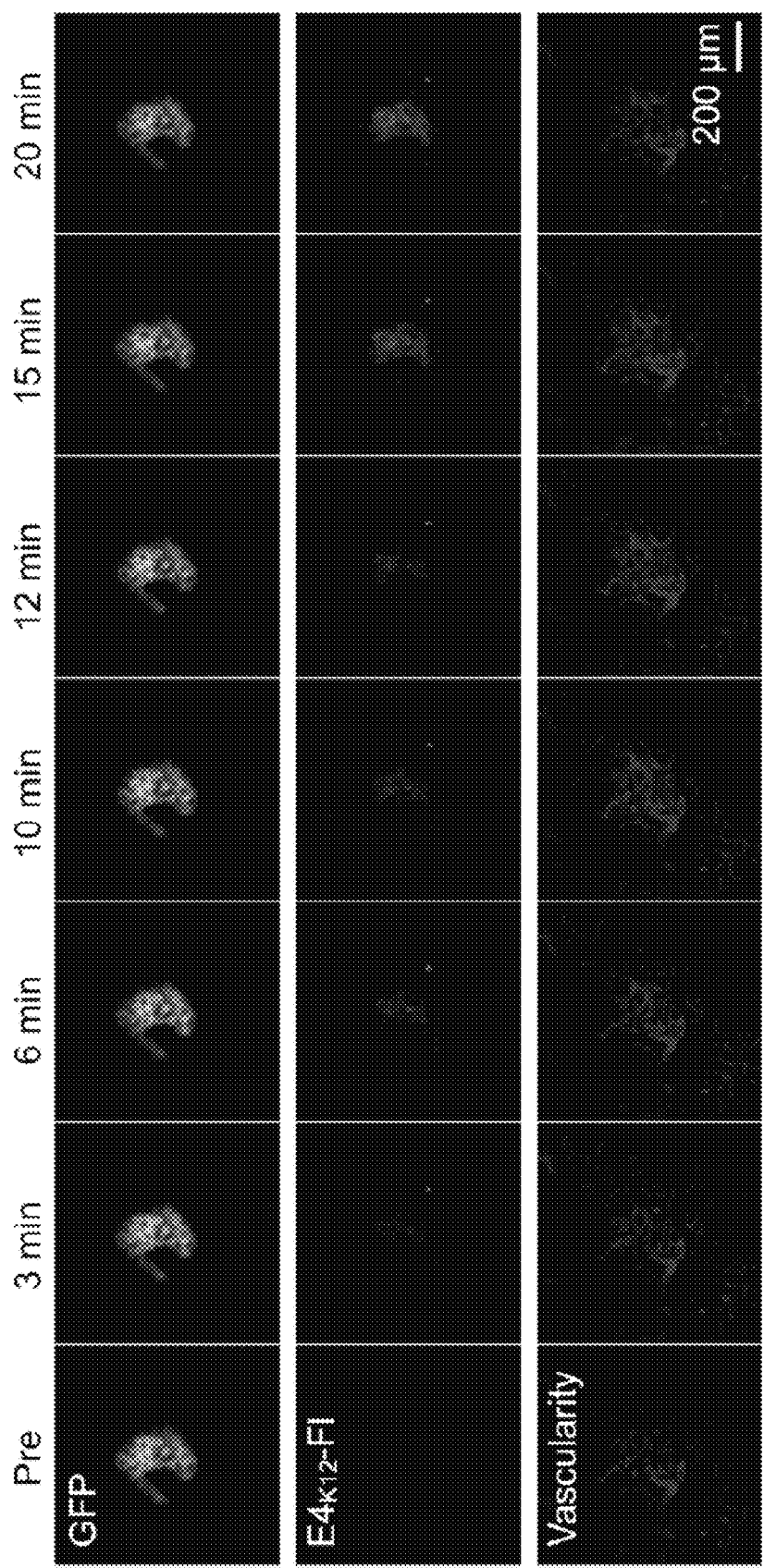
FIG. 7 is a fluorescence image of in vivo time course imaging of probe accumulation in an islet. GPF channel (488 nm) fluorescence images are depicted in the top row; Exendin-4$_{K12}$ conjugated to VT680 channel (680 nm) fluorescence images are depicted in the middle row, and vasculature (750 nm) fluorescence images are depicted in the bottom row (all images with 10× objectives; scale bar: 200 μm).
Figure 8:
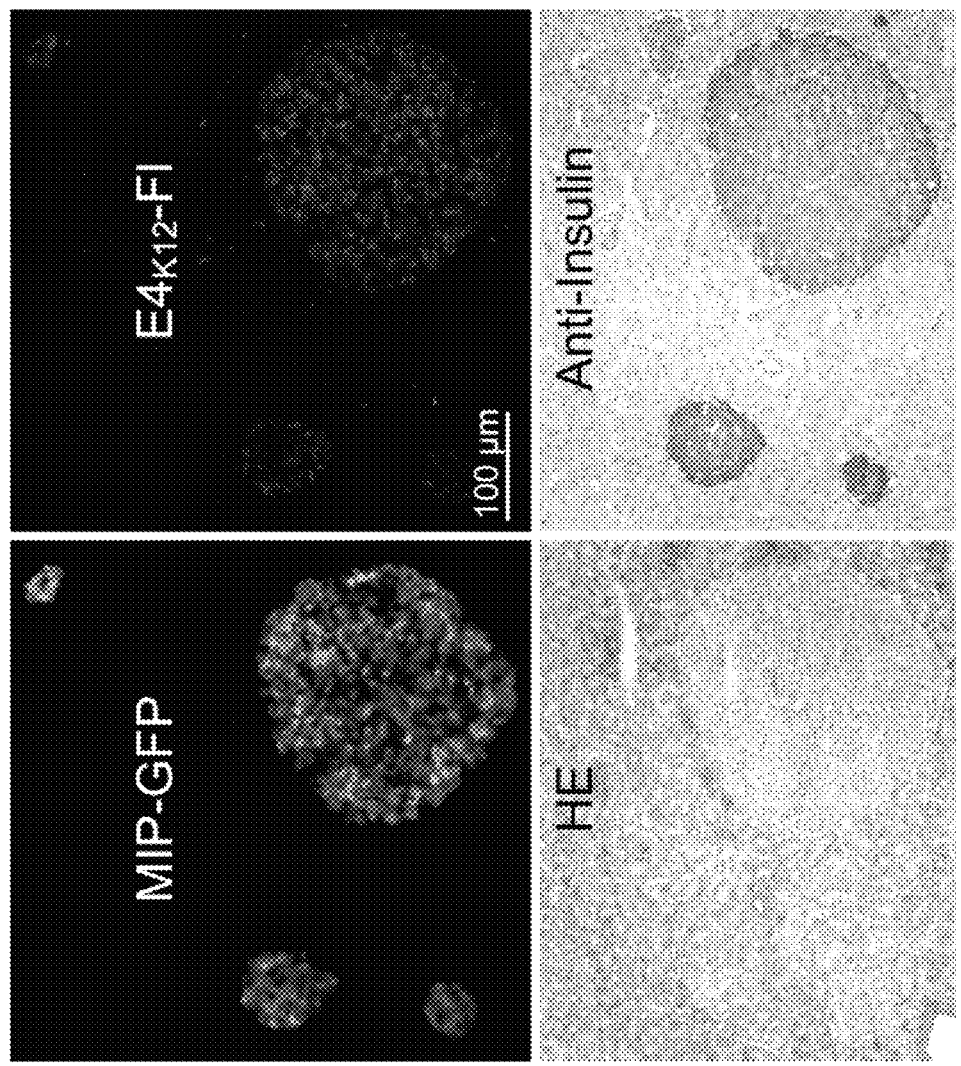
FIG. 8 is a fluorescence image of in vivo time course of the conjugate accumulation in an islet. GPF channel (488 nm) fluorescence images are depicted in the top row; Exendin-4$_{K12}$ conjugated to VT680 channel (680 nm) fluorescence images are depicted in the middle row, and vasculature (750 nm) fluorescence images are depicted in the bottom row (all images with 10× objectives; scale bar: 200 μm).

In order to evaluate the performance of Exendin-$4_{K12}$-VT680 in vivo, NOD MIP-GFP mice were anesthetized and the pancreas exteriorized onto a heated chamber for real-time multi-channel confocal imaging. Microvasculature was imaged in the 750 nm channel after injection of AngioSense-780, a long circulating blood pool agent, and islets were identified in the 488 nm channel via their GFP expression. Following this, 8 nmol of Exendin-$4_{K12}$-VT680 in 200 µL of PBS was injected, and accumulation of the probe in the islets and surrounding tissue was monitored (FIG. 6). Intravital imaging confirmed that prior to imaging no signal corresponding to a pancreatic islet was observable in the Exendin-$4_{K12}$-VT680 channel (FIG. 7, 0 min). However, after 3 minutes, accumulation of $E4_{K12}$-Fl could be observed in the pancreatic islets, and this fluorescence increased during the observation time of 20 minutes, after which steady state was reached (Target-to-background ratio of 6:1; FIG. 7). Ninety minutes after injection, the signal displayed still a ratio of 6:1. On comparison of imaging results from the vasculature and GFP-islets, it was confirmed that Exendin-$4_{K12}$-VT680 co-localized in the pancreatic beta cells, and did not simply extravasate from the vasculature that traverses the islets. During the time of measurement, no increase in background noise from surrounding tissue was observed. The target-to-background ratio of islets over exocrine pancreas was 6.0±0.5 in steady state. To further confirm that probe accumulation occurs in pancreatic beta cells, additional immuno- and fluorescence histology was performed (FIG. 8). These studies also demonstrated exclusive accumulation of Exendin-$4_{K12}$-VT680 in the islets and specifically in the pancreatic beta cells expressing insulin and GLP-1R. Biodistribution studies showed renal excretion of non-localized agent and intracellular degradation in endosomal compartments.

Example 6. In Vivo Quantification of Beta Cell Mass Using Exendin-$4_{X12}$-VT750

Animals

Both C57BL/6J (B6) mice and B6.Cg-Tg(Ins1-EGFP) 1Hara/J mice (38), which express the green fluorescent protein eGFP within the islets under the mouse insulin 1 promoter (MIP-GFP), were obtained from The Jackson Laboratory (Bar Harbor, Me.). All procedures and animal protocols were approved by the subcommittee on Research Animal Care at Massachusetts General Hospital.

Animal Preparation

Mice were anesthetized with 2% isoflurane and 2 L/minute $O_2$. The peritoneal cavity was opened with a transverse incision in the disinfected abdominal wall. The gastric-splenic ligament was then dissected and the pancreas carefully exteriorized for intravital microscopy. Robust blood flow was observed in the pancreatic arteries for the duration of each experiment, and pancreas perfusion was confirmed by the presence of a circulating fluorescent vascular agent (Angiosense 680, PerkinElmer, Waltham, Mass.). The exteriorized pancreas was then completely submerged in temperature-controlled lactated Ringer's solution. The temperature near the spleen was carefully monitored using an Omega HH12A thermometer with fine wire thermocouples (Omega Engineering Inc., Stamford, Conn.) and maintained at 37° C. A tail vein catheter, made using a 30 G×½" needle inserted into CLAY ADAMS® Polyethylene10 tubing, was inserted prior to surgery. Via this tail vein catheter, 200 µL (2 to 4 nmol/200 µL) of Exendin-$4_{X12}$-VT750 was subsequently injected either with or without pre-injection of Exendin-4 (15 nmol/200 µL).

Intravital Laser-Scanning Microscopy

Images were collected with an intravital laser-scanning microscope (IV100, Olympus Corporation, Tokyo, Japan) using an Olympus 20× (UplanFL N.A. 0.5) objective. Samples were excited at 488 nm with an air-cooled argon laser (Melles Griot, Carlsbad, Calif.) for visualization of either GFP-expressing islet-cells or cells stained with Celltracker Green CMFDA (Invitrogen, Carlsbad, Calif.). The samples were also excited at 748 nm with a red diode laser (Model FV10-LD748, Olympus Corporation, Tokyo, Japan) for visualization of Exendin-4$_{x12}$-VT750. Light was collected using custom-built dichroic mirrors SDM-560 and SDM-750, and emission filters BA 505-550 and BA 770 nm IF (Olympus Corporation, Tokyo, Japan). The green and red signals were collected sequentially to avoid bleed-through into the VT750 channel. A prototypical tissue stabilizer (Olympus Corporation, Tokyo, Japan) was used to reduce motion artifacts and to stabilize the focal plane. The stabilizer was attached to the objective and its z-position was finely adjusted using a micrometer screw to apply soft pressure on the tissue.

Image Analysis

The accumulation of the Exendin-4$_{x12}$-VT750 probe within islets was determined by intravital imaging in mouse insulin promoter-green fluorescent protein (MIP-GFP) mice, as described above, using an Olympus UPlanFl 10× (NA 0.3) objective. Images prior to probe injection were collected from islets showing a robust MIP-GFP signal and apparently intact vasculature, immediately following intravenous tail-vein injection of E4$_{x12}$-VT750 (0.2 nmol/g in 200 μL of a 10 μM solution, PBS). This dose was determined by fluorescence dose response experiments for the fluorochrome chosen. Regions of interest (ROIs) were drawn within and outside the islets and temporal changes were plotted using Prism 5.0a (GraphPad Software La Jolla, Calif.). Ex vivo ROIs were determined using pancreata that were excised 1 hour after IV injection of the Exendin-4$_{x12}$-VT750 probe into MIP-GFP mice.

Immunohistochemistry and Beta Cell Mass Estimation

The pancreata were embedded in OCT compound (Sakura Finetek, CA) and flash-frozen in an isopentane bath on dry ice. The frozen tissues were sectioned (thickness: 5 μm), mounted on microscope slides and stored at −80° C. For insulin immunohistochemistry, the tissue sections were pre-incubated with 0.3% $H_2O_2$ to suppress endogenous peroxidase activity and then blocked with 5% normal goat serum in PBS. Following the addition of a rabbit polyclonal insulin antibody (insulin H-86: Santa Cruz Biotechnology, CA), a biotinylated anti-rabbit secondary antibody (Vector Laboratories Inc., CA) was applied. The Vectastain ABC kit (Vector Laboratories Inc., CA) and a 3-amino-9-ethylcarbazole (AEC) substrate (Dako, CA) were then used for color development. All the sections were counterstained with Harris hematoxylin solution. For overall morphology, hematoxylin and eosin (H&E) staining was also performed, and all images were captured using NanoZoomer 2.0RS (Hamamatsu, Japan). Beta cell mass was determined by thresholding and quantitating insulin positive areas in non-adjacent sections at 50 m intervals throughout pancreata and corroborated by insulin stains according to published protocols (Montanya et al. *Methods Mol Biol* 560:137-158, 2009). All images were digitized using a NanoZoomer 2.0RS (Hamamatsu, Japan). Color deconvolution was based on orthonormal transformation of the original RGB image. For each cohort, we analyzed a minimum of 15 individual whole pancreatic histological slides (3 sections for each sample) containing approximately 40,000×40,000 pixels per image. Image processing was done using Matlab software.

Fluorescence Microscopy of Histological Slides

Fluorescence microscopy was performed at different wavelengths on the same sections of pancreata. GFP fluorescence was observed using a Chroma HQ FITC filter cube (HQ480/40×EX, dichroic Q505LP BS, and emission filter HQ535/50m EM), whereas, Exendin-4 VT750 fluorescence was observed using a Chroma Cy7 filter cube (HQ775/50× EX, dichroic Q810LP BS, and emission filter HQ845/55m EM; Chroma Technology Corp., VT, USA). All images were captured and processed using an epifluorescence microscope, Nikon Eclipse 80i (Nikon Instruments Inc., NY), with a Cascade Model 512B camera (Roper Scientific, Arizona).

Streptozotocin-Treatment

Two cohorts of B6 mice at 14 to 18 weeks of age received intraperitoneal injections of streptozotocin (STZ, Sigma-Aldrich, St. Louis, Mo.) dissolved in 0.1M sodium citrate (pH=4.5); mice received either a single injection of 75 mg/kg or 150 mg/kg body weight respectively or 100 mg/kg STZ daily for 5 days. Mice were given access to 10% glucose-enriched water overnight to avoid hypoglycemia post-injection. Five days following STZ treatment, fluorescence- and histology-based whole pancreas islet quantification was performed. Blood-glucose levels from the tail-vein were measured using the Contour® Blood Glucose Monitoring System (Bayer HealthCare LLC, Mishawaka, Ind.).

Fluorescence-Based Whole Pancreas Islet Quantification

After IV injection of Exendin-4$_{x12}$-VT750 (200 μL, 10 μM) and a 40-minute time interval, untreated and STZ-treated mice were injected with heparin (approximately 3 units of heparin, 300 μL of a 10 USP/mL solution) 10 minutes before euthanasia by $CO_2$ asphyxiation. B6 mice used for blocking experiments were injected with Exendin-4 (250 μL, 60 μM, 20-minute time interval) prior to injection with Exendin-4$_{x12}$-VT750 (200 μL, 10 μM, IV, 40-minute time interval) and then heparin (approximately 3 units of heparin, 300 μL of a 10 USP units/mL solution) 10 minutes before euthanasia by $CO_2$ asphyxiation. The mice were then immediately perfused with 30 mL of PBS and heparin via the left ventricle. Likewise, 5 mL of PBS-heparin was perfused through the splenic artery in order to completely flush the pancreas. The organ was then excised, weighed, and placed between two cover glass slides using a 1 mm rubber gasket to maintain a constant thickness. Fluorescence reflectance imaging of the entire pancreas was performed using an OV110 epifluorescence imager (Olympus; Center Valley, Pa.) at low magnification (0.14×), equipped with standard filters for the 750 nm channel, and a 2-second exposure. An ROI was drawn around the edges of the pancreas, and the average fluorescence signal was calculated using ImageJ (NIH, USA). For each cohort of mice, the autofluorescence signal in the pancreas was subtracted from both mice receiving injections of only Exendin-4$_{x12}$-VT750 as well as from the respective mice injected with both Exendin-4$_{x12}$-VT750 and Exendin-4; specific uptake was then determined by subtracting one from the other.

Laparoscopic Islet Imaging

Mouse pancreata were also imaged with a fiber-optic catheter-based imaging system in live mice using a laparoscopic approach; similar systems are used microendoscopic purposes such as imaging through the pancreatic duct in humans. The in-house designed imaging system includes a 1.6 mm outer diameter fiber-optic catheter, and a 0.9 mm working channel coupled to an optical collection setup containing two high-resolution cameras (Pixelfly; PCO, Germany). Using this system, light collected from the fiber-optic catheter is divided into discrete white light and near infrared (NIR) beams by a 45-degree dichroic mirror. These beams are then focused onto the cameras, which enable simultaneous NIR (excitation/emission 747/780-820 nm) and white light imaging. To perform islet imaging, animals were anesthetized with 2% isofluorane in 1 L/minute $O_2$, and fixed in a supine position with tape. The pancreas and surrounding organs were then surveyed using the fiber-optic catheter, in a similar manner to laparoscopic clinical procedures. Finally, the scanned area was also imaged using a confocal laser microscope (IV100, Olympus Corporation, Tokyo, Japan), operating at 2 different optical channels (488 nm excitation for MIP-GFP and 748 nm excitation for $E4_{X12}$-VT750). This was used to confirm that the observed fluorescent areas did indeed colocalize with MIP-GFP expressing cells.

Pharmacokinetics

Figure 9E:
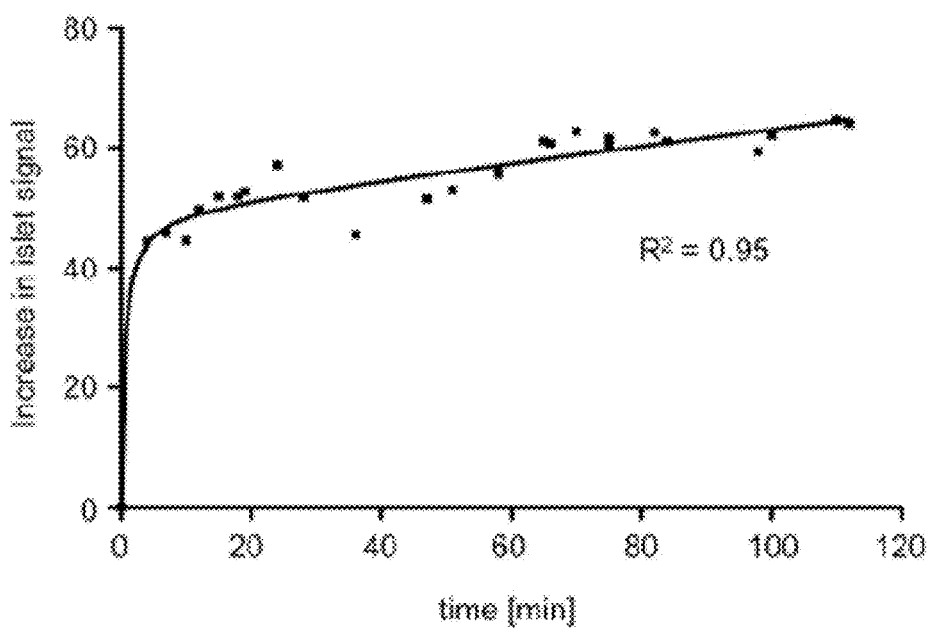
FIG. 9E is a line graph of the increase in islet signal following a dose of systemic Exendin-4$_{X12}$ conjugated to VT750 injection.
Figure 9F:
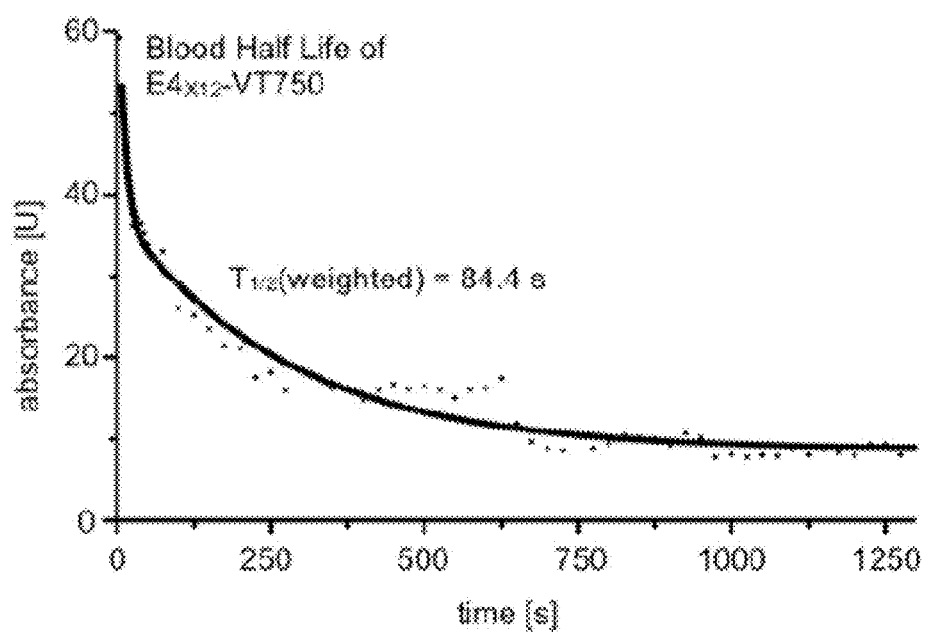
FIG. 9F is a line graph of the blood half-life measurement of Exendin-4$_{X12}$ conjugated to VT750 (0.2 nmol/g) injected into a MIP-GFP mouse (scale bar: 100 μm).

Under in vivo conditions, Exendin-$4_{X12}$-VT750 accumulated rapidly and selectively in both islets and beta cells, as confirmed by co-localization with the MIP-GFP signal (FIGS. 9A-D). Pancreata of live MIP-GFP mice were then exteriorized and intact blood flow confirmed through an injection of Angiosense 680. After focusing on an islet, mice were injected with Exendin-$4_{X12}$-VT750 (2 to 4 nmol/200 µL) and islet signal intensity was measured over time. Exendin-$4_{X12}$-VT750 was seen to accumulate in pancreatic beta cells within 10 minutes, reaching a plateau at ~15 minutes (FIG. 9E). At 2 hours after injection the islet signal had increased approximately 64 fold over background. The blood concentration of Exendin-$4_{X12}$-VT750 followed a biexponential decay, giving a weighted $T_{1/2}$ of 84.4 seconds (FIG. 9F).

The organ distribution of Exendin-$4_{X12}$-VT750 was estimated by measuring the 750 nm fluorescence in excised organs (mean fluorescence units (MFU)×$A^2$), and comparing them 60 minutes after IV injection to the autofluorescence of non-injected normal mice. The comparative fluorescence distribution was as follows: kidney (69.0%), liver (14.8%), pancreas (7.9%), intestine (3.7%), lungs (2.6%) and stomach (1.7%). The NIR fluorophore uptake in both the spleen and heart was <1%. Serial imaging data suggested that the primary excretion pathway for Exendin-$4_{X12}$-VT750 was predominantly renal, based on the high quantities of probe in the bladder and kidney; this is consistent with the compound's size and blood half-life.

Validation

Figure 10A:
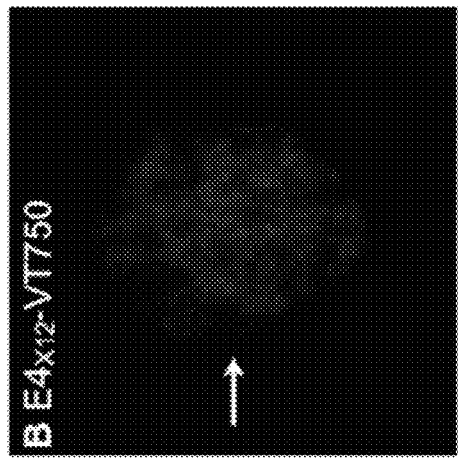
FIG. 10A is a fluorescence image of a single islet in an MIP-GFP mouse.
Figure 10B:
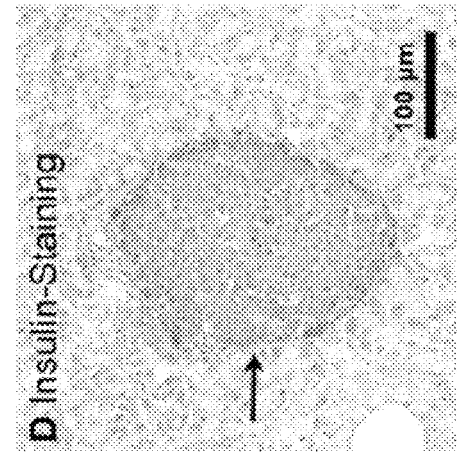
FIG. 10B is a fluorescence image of a single islet in an MIP-GFP mouse injected with Exendin-4$_{X12}$ conjugated to VT750.
Figure 10C:
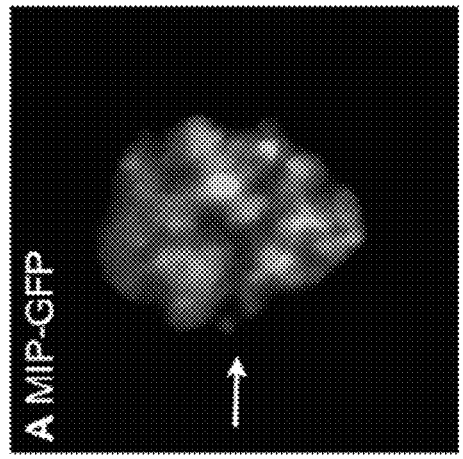
FIGS. 10C and 10D are images of a single islet with H&E-staining and insulin-staining, respectively.
Figure 10D:
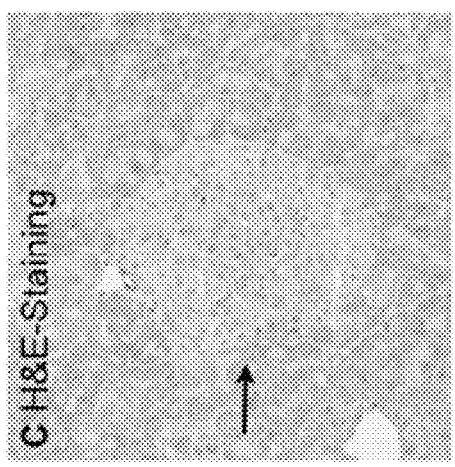
Figure 10E:
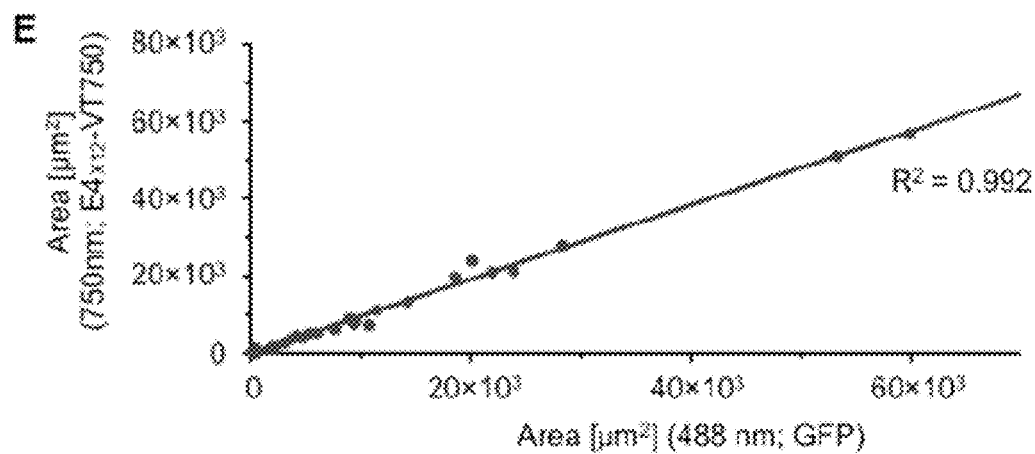
FIG. 10E is a line graph of the correlation of islet sizes estimated via the MIP-GFP reporter (488 nm) versus the GLP-1R probe Exendin-4$_{X12}$ conjugated to VT750 fluorophore (750 nm).
Figure 10F:
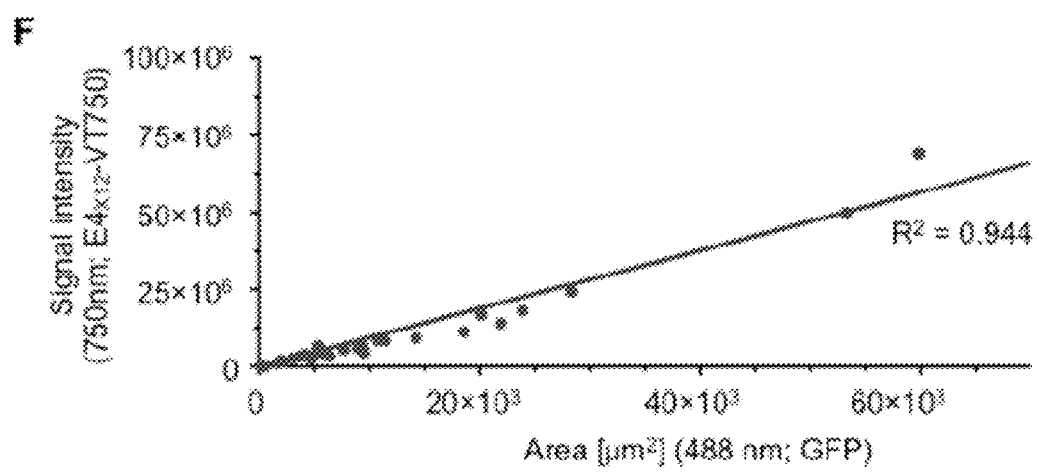
FIG. 10F is a line graph of the correlation of islet sizes observed with the MIP-GFP reporter (488 nm) versus signal intensity observed at 750 nm in the same area.

To quantitatively correlate probe uptake in pancreatic beta cells, image analysis of MIP-GFP mice was performed. Mice were sacrificed 40 minutes after IV injection of the probe, and their pancreata were removed and sectioned for imaging. Signal in the 488 nm channel (FIG. 10A) represented insulin-promoter-driven GFP expression, an indicator of islet area, while signal in the 750 nm channel (FIG. 10B) read out probe uptake. FIGS. 10C and 10D show the hematoxylin and eosin staining and anti-insulin staining of an adjacent histological slide, respectively. There was an excellent correlation between the islet sizes determined by areas in the GFP and VT750 channels (FIG. 10E, $R^2$=0.992). A similar excellent correlation between Exendin-$4_{X12}$-VT750 signal intensities and islet areas estimated from GFP expression was found (FIG. 10F, $R^2$=0.944). When mice were injected with unlabeled exendin-4 (15 nmol) prior to injection with Exendin-$4_{X12}$-VT750 (2 nmol), however, no uptake of imaging agent was observed in pancreatic beta cells. This therefore confirmed the selective binding of the fluorescent reporter to GLP-1 receptors in vivo.

Loss of Beta Cell Mass

Figure 11D:
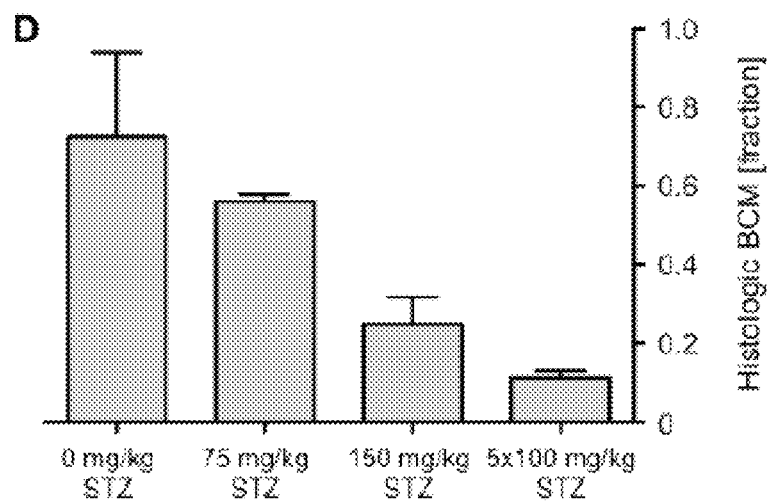
FIG. 11D is a bar graph of beta cell mass, as estimated from histology of untreated mice and mice treated with different concentrations of STZ.
Figure 11E:
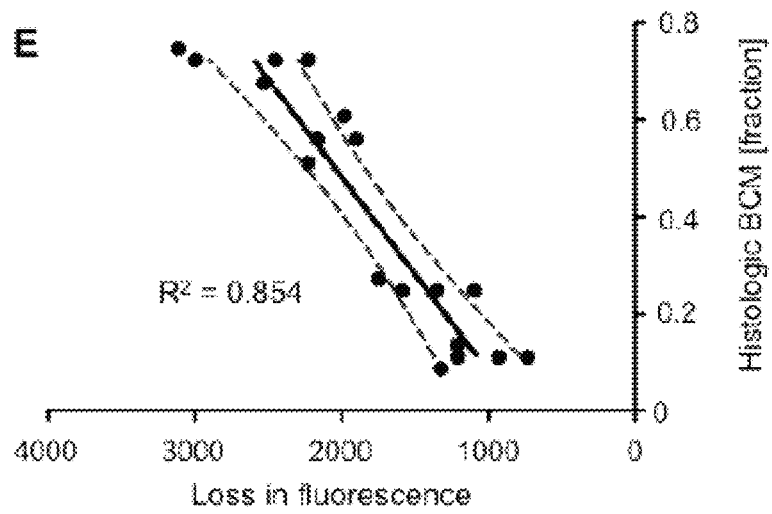
FIG. 11E is a line graph of the correlation of beta cell mass quantification data from immunohistochemical staining and from Exendin-4$_{X12}$-VT750 fluorescence measurements.

To determine whether the probe could also be used to measure loss of beta cell mass, Exendin-$4_{X12}$-VT750 accumulation (measured via whole-pancreas imaging) and beta cell mass (quantified by histology) were compared, with and without STZ administration to B6 mice. STZ rather specifically kills pancreatic islet beta cells, eventually resulting in insulin-dependent diabetes. FIGS. 11A and 11B show representative examples of islets and surrounding exocrine pancreas tissue at two different resolutions, illustrating that Exendin-$4_{X12}$-VT750 stains pancreatic islets with high specificity. FIG. 11C summarizes image analysis from various cohorts of mice treated with different amounts of STZ. The NIR fluorescence decreased with increasingly aggressive STZ treatment. Mice were normoglycemic (blood-glucose levels <250 mg/dL) at the lowest STZ dose and hyperglycemic at the higher doses (FIG. 11C). When compared with immunohistochemical estimation of beta cell mass via anti-insulin staining (FIGS. 11D and 11E), there was a good correlation between observed fluorescence intensity for Exendin-$4_{X12}$-VT750 and beta cell mass ($R^2$=0.854; P<0.0001; FIG. 11E). These data show that probe accumulation correlates with beta cell mass and is sensitive enough to detect a beta cell mass loss in mice that are still normoglycemic (a<25% loss of beta cell mass is detectable at 99% confidence interval; FIG. 11E).

Fiber-Optic Imaging

Figure 12A:
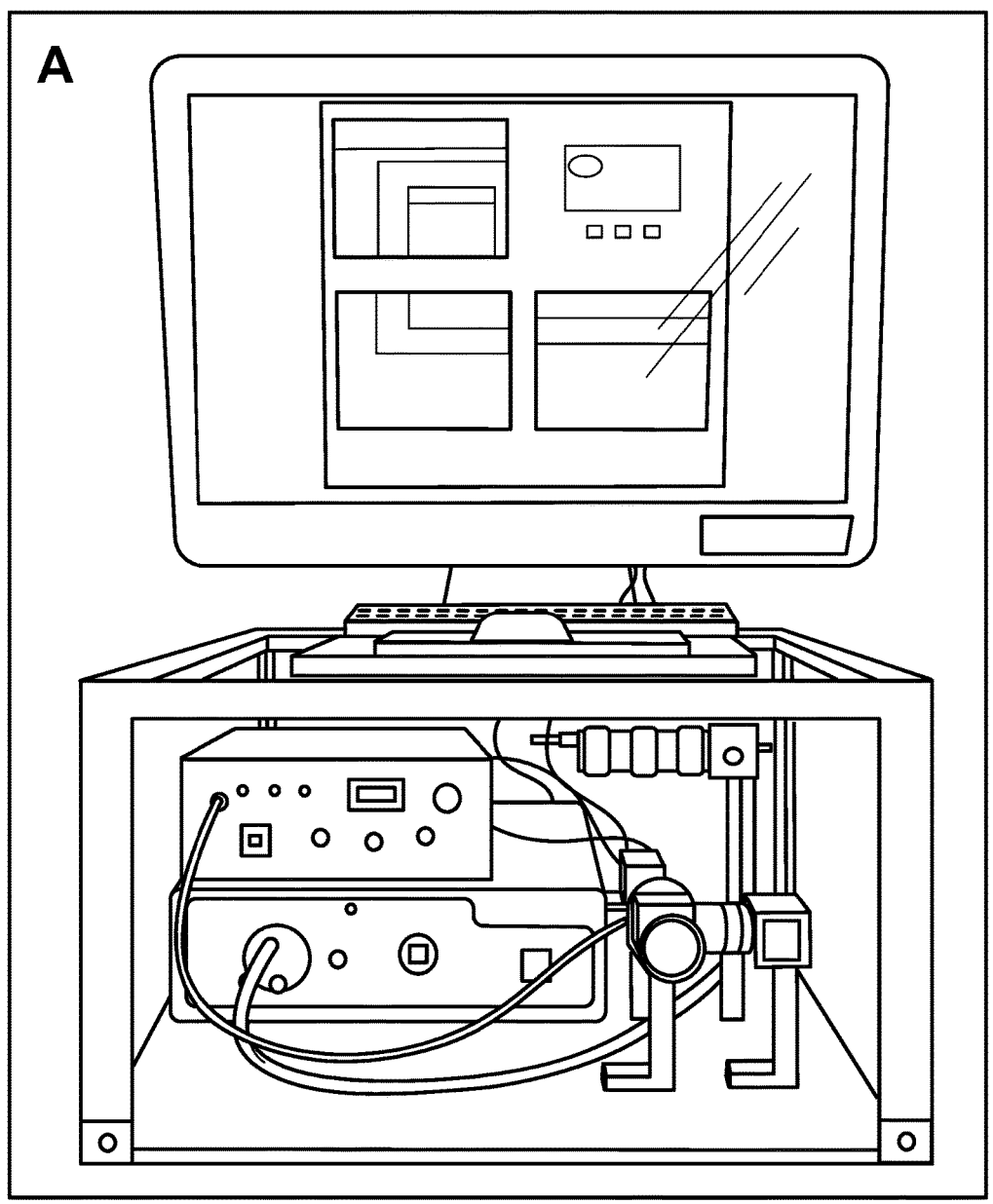
FIG. 12A is a drawing of an intravital imaging system.
Figure 12B:
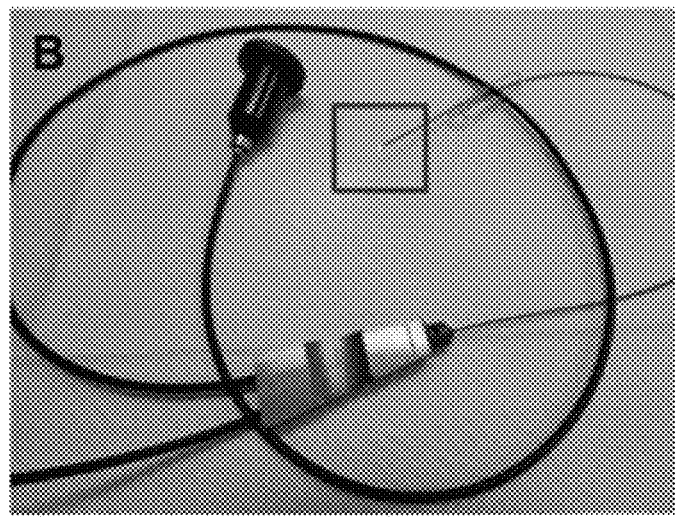
FIG. 12B is a photographic image of an endoscopic imaging probe.
Figure 12C:
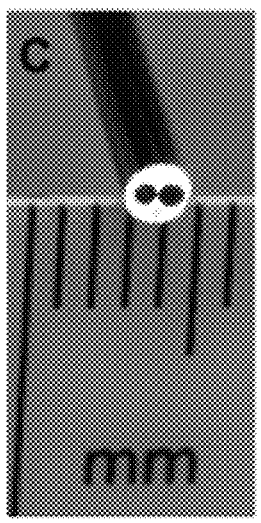
FIG. 12C is a photographic image of the imaging probe head (outer diameter: 1.6 mm, probe head indicated in FIG. 12B by box).
Figure 12D:
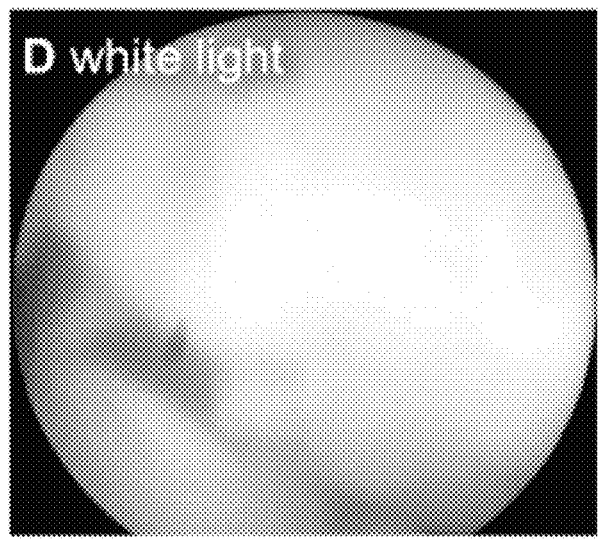
FIG. 12D is an image of the field of view under white light conditions.
Figure 12E:
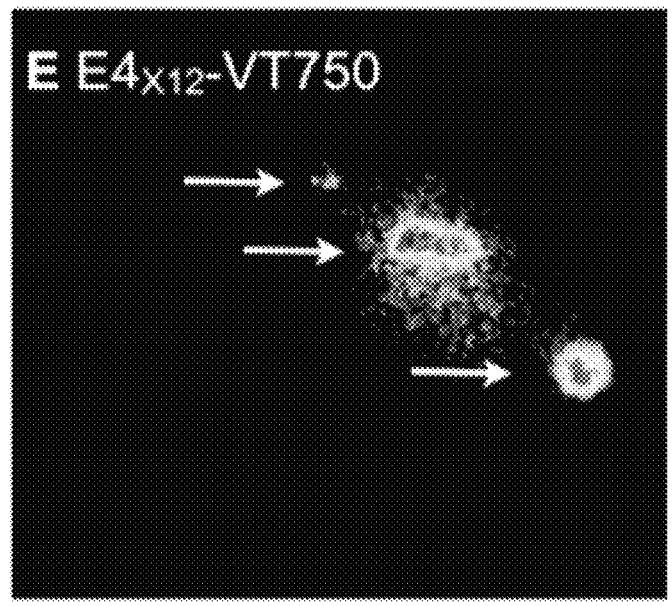
FIG. 12E is an image of near infrared (NIR) signal in islets of the same area as in FIG. 12D.
Figure 12F:
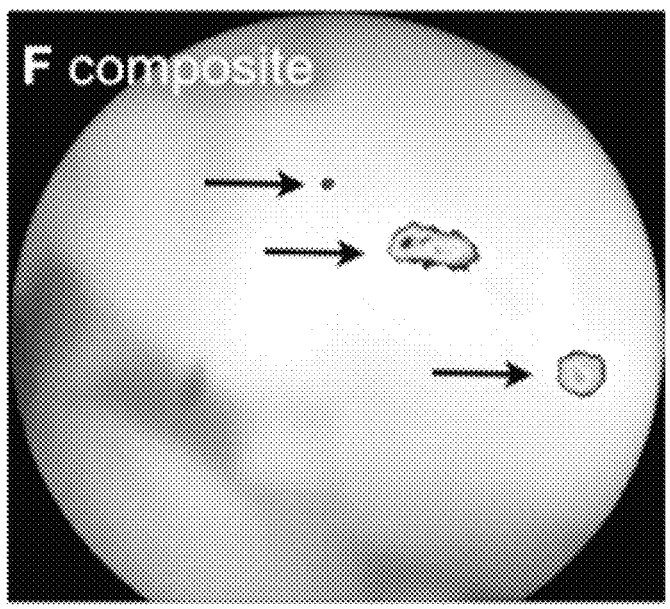
FIG. 12F is a composite image of the images depicted in FIGS. 12D and 12E.

To test the feasibility of fiber-optic islet imaging and/or confocal microscopy endoscopic imaging, the probe in live mice using a custom-built, single channel (680 nm) microendoscopic imaging system was tested (FIGS. 12A-C). MIP-GFP mice were injected with Exendin-$4_{X12}$-VT750 via tail vein (0.2 nmol/g), and their pancreata were examined. The results showed that the NIR fluorescence signal could be clearly detected, and was co-localized with the GFP signal using a separate confocal microscope but having 2 optical channels (480 and 680 nm; FIGS. 12D-F). This system could thus potentially be used in endoscopic (i.e imaging pancreatic parenchyma through duodenal sweep or via pancreatic duct), laparoscopic or intraoperative settings to map surface located islets.

Example 7. Preparation and Characterization of an Exendin-4-$^{18}$F Labelled Conjugate During earlier studies (Reiner et al. *Bioconjug Chem* 21: 1362-1368, 2010), the Lys12 amino acid of Exendin-4 (FIG. 13A) was identified to be an ideal attachment point for near infrared fluorophores. Attachment at this site does not perturb the ability of Exendin-4 derived amino acid sequences to strongly and selectively bind to GLP1 receptors.

To facilitate non-invasive whole pancreas imaging of pancreatic beta cells, the synthesis of a $^{18}$F-exendin-4 derived amino acid sequence was envisioned, which could be synthesized based on reported fast and selective labeling strategies (Keliher et al. Chem. Med. Chem. 6: 424-427, 2011; Reiner et al. *Angew Chem Int Ed Engl* 50: 1922-1925, 2011). Thus, an Exendin-4 based amino acid sequence where the Lys12 was replaced with a cysteine (Exendin-$4_{C12}$) was synthesized, thus enabling the selective and covalent modification of the thiol-moiety with a maleimide-tetrazine ($E4_{Tz12}$, FIGS. 13B and 13C).

Synthesis of the Exendin-4-$^{18}$F Labelled Conjugate

The synthesis of novel maleimide-tetrazine crosslinker 3 was conducted using standard amide coupling conditions (EDCI, $Et_3N$, RT, (DCM). The synthesis of the tetrazine-modified exendin-4 probe $E4_{Tz12}$ 4 was performed in PBS buffer (pH=7.2) and at room temperature. Finally, the bioorthogonal conjugation of the tetrazine 4 with the $^{18}$F functionalized trans-cyclooctene was performed under aqueous conditions employing DMSO and $H_2O$ at room temperature.

Characterization of the Exendin-4-$^{18}$F Labelled Conjugate

Figure 14A:
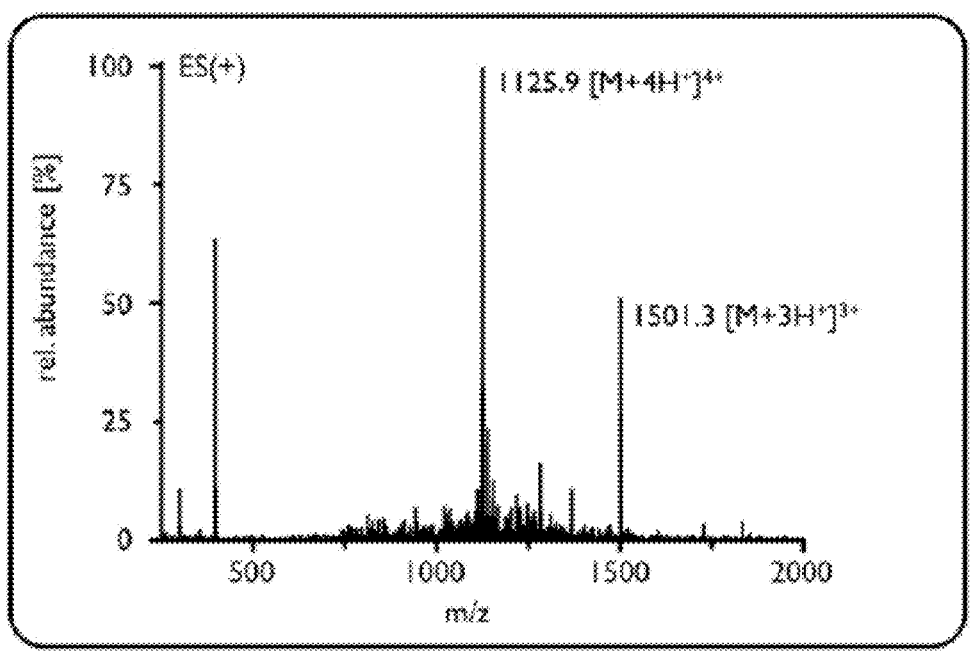
FIGS. 14A and 14B are images of electrospray ionization liquid chromatography/mass spectrometry (ESI LC/MS) of Exendin-4$_{Tz12}$ of the positive polarization and the negative polarization, respectively.
Figure 14B:
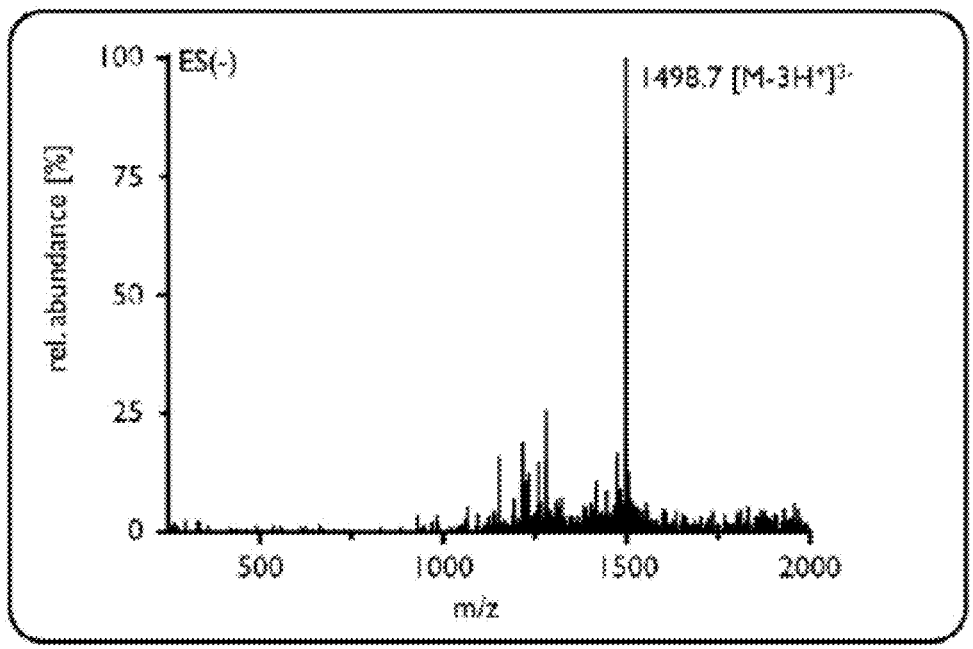

FIGS. 14A and 14B show the positive polarized (FIG. 14A) and negative polarized (FIG. 14B) ESI LC/MS spectra of Exendin-4$_{Tz12}$. This modification allowed the conversion of the resulting Exendin-4$_{Tz12}$ with $^{18}$F-TCO or the non-radioactive equivalent, $^{19}$F-TCO. The resulting $^{18}$F-labeled peptide Exendin-4$_{TzTCO12}$-$^{18}$F was purified using TCO-scavenger beads and 3 kDa cut off filters, yielding the pure compound in 82% dcRCY (FIGS. 14A and 14C).

Figure 15A:
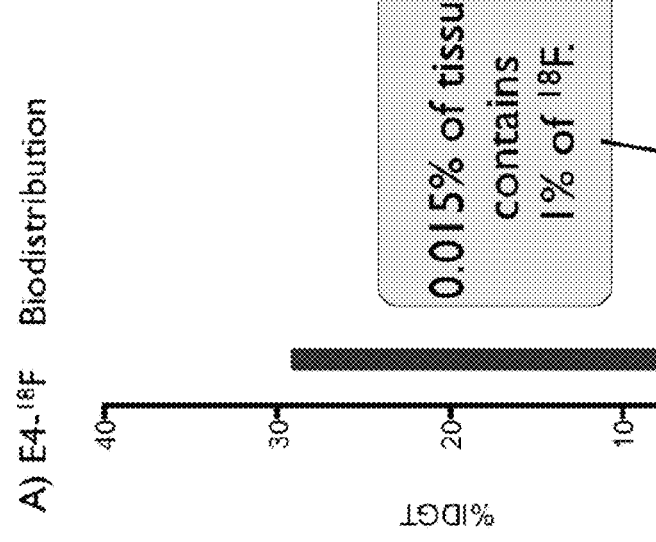
FIG. 15A is a bar graph of the biodistribution of Exendin-4 conjugated to $^{18}$F in B6 mice.
Figure 15B:
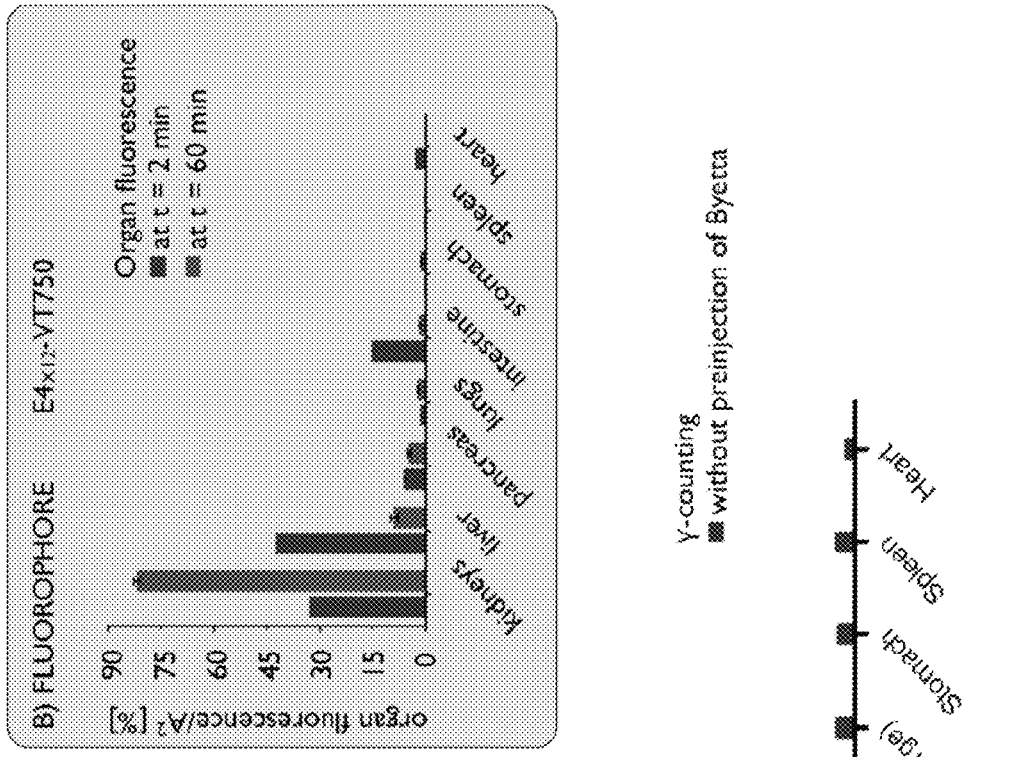
FIG. 15B is a bar graph of the biodistribution of Exendin-4$_{X12}$ conjugated to VT750 in B6 mice.

Example 8. In Vivo Assessment of Biological Distribution of Exendin-4-$^{18}$F Labelled Conjugate To assess the biological distribution of the Exendin-4-$^{18}$F, 50 μCi of E4$_{TzTCO12}$-$^{18}$F were injected into B6 mice (n=3), the mice sacrificed after 60 minutes, organs excised and the distribution of E4$_{TzTCO12}$-$^{18}$F analyzed using γ-counting (FIG. 15A). The distribution of E4$_{TzTCO12}$-$^{18}$F was comparable to that of the NIR fluorescently labeled peptide E4$_{X12}$-VT750 (FIG. 15B). Although the total uptake of $^{18}$F was just above 1% of the injected dose, the quantity of the accumulated material was remarkable, given the fact that pancreatic beta cells accounted for just about 0.015% of the total mouse tissue. Taking the mass of the targeted organ into account, the pancreatic beta cells had the highest uptake of E4$_{TzTCO12}$-$^{18}$F of all displayed tissues.

To assess the selectivity of the $^{18}$F-modified peptide, 50 μCi of E4$_{TzTCO12}$-$^{18}$F were injected into MIP-GFP mice (n=3) which express the green fluorescent protein (GFP) under the mouse insulin promoter (MIP), therefore making the pancreatic beta cells detectable via their green fluorescence. Colocalization of the green fluorescent signal in the GFP channel (FIG. 16A) and autoradiography analysis (FIG. 16B) showed remarkable colocalization of fluorescence and activity which did not align with the pancreatic tissue (FIG. 16C). This was understandable since the pancreatic islets are not evenly dispersed in the pancreas.

Confirmation of a) the fact that E4$_{TzTCO12}$-$^{18}$F colocalized with pancreatic beta cells and b) its high specific uptake in beta cells confirmed the results obtained for NIR labeled fluorescent probes, making E4$_{TzTCO12}$-$^{18}$F the first $^{18}$F-labeled GLP1R targeting probe for pancreatic beta cells.

What is claimed is:

1. A composition comprising the peptide sequence SEQ ID NO:3, wherein the amino acid at position 12 is cysteine.

2. The composition of claim 1, wherein the cysteine is modified with a linker comprising a maleimide at a first end and a tetrazine at a second end.

3. The composition of claim 2, wherein the cysteine reacts with the maleimide via a 1,2-addition reaction.

4. The composition of claim 2, wherein the tetrazine reacts with a strained alkene attached to a detectable agent via an inverse electron demand Diels-Alder reaction.

5. The composition of claim 4, wherein the strained alkene is trans-cyclooctene.

6. The composition of claim 4, wherein the detectable agent comprises a fluorophore, a radioactive isotope, or a paramagnetic element.

7. The composition of claim 6, wherein the detectable agent is a fluorophore.

8. The composition of claim 7, wherein the fluorophore is VT-680 or VT-750.

9. The composition of claim 6, wherein the detectable agent is a radioactive isotope.

10. The composition of claim 9, wherein the radioactive isotope is suitable for PET imaging.

11. The composition of claim 9, wherein the radioactive isotope is suitable for SPECT imaging.

12. The composition of claim 9, wherein the radioactive isotope is selected from the group consisting of fluorine-18, carbon 11, nitrogen-13, zirconium-89, copper-64, gallium-67, technetium-99m, indium-111, iodine-123, xenon-133, and thallium-201.

13. The composition of claim 9, wherein the radioactive isotope is flourine-18.

14. The composition of claim 6, wherein the detectable agent is a paramagnetic element.

* * * * *

UNITED STATES PATENT AND TRADEMARK OFFICE
CERTIFICATE OF CORRECTION

PATENT NO. : 9,999,689 B2
APPLICATION NO. : 15/076466
DATED : June 19, 2018
INVENTOR(S) : Ralph Weissleder, Thomas Reiner and Edmund J. Keliher Page 1 of 1

It is certified that error appears in the above-identified patent and that said Letters Patent is hereby corrected as shown below:

On the Title Page

Item (*) Notice, Line 3, after "0 days." delete "days."

In the Specification

In Column 1, Line 7, delete "Sep. 9," and insert -- Oct. 30, --

In the Claims

In Column 32, Line 51, Claim 12, delete "carbon 11" and insert -- carbon-11 --

In Column 32, Line 55 (approx.), in Claim 13, delete "flourine" and insert -- fluorine --

Signed and Sealed this
Nineteenth Day of May, 2020

Andrei Iancu
*Director of the United States Patent and Trademark Office*

SEQUENCE LISTING

```
<160> NUMBER OF SEQ ID NOS: 5

<210> SEQ ID NO 1
<211> LENGTH: 39
<212> TYPE: PRT
<213> ORGANISM: Homo sapiens

<400> SEQUENCE: 1

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser
        35

<210> SEQ ID NO 2
<211> LENGTH: 39
<212> TYPE: PRT
<213> ORGANISM: Artificial Sequence
<220> FEATURE:
<223> OTHER INFORMATION: Synthetic Peptides
<220> FEATURE:
<221> NAME/KEY: Non-natural amino acid
<222> LOCATION: 12
<223> OTHER INFORMATION: (S)-2-amino-4-pentynoic acid

<400> SEQUENCE: 2

His Gly Glu Gly Thr Phe Thr Ser Asp Leu Ser Xaa Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser
        35

<210> SEQ ID NO 3
<211> LENGTH: 39
<212> TYPE: PRT
<213> ORGANISM: Artificial Sequence
<220> FEATURE:
<223> OTHER INFORMATION: Synthetic Peptides

<400> SEQUENCE: 3
```

-continued

```
His Gly Glu Gly Thr Phe Thr Ser Asp Leu Ser Cys Gln Met Glu Glu
1               5                   10                  15

Glu Ala Val Arg Leu Phe Ile Glu Trp Leu Lys Asn Gly Gly Pro Ser
                20                  25                  30

Ser Gly Ala Pro Pro Ser
            35

<210> SEQ ID NO 4
<211> LENGTH: 30
<212> TYPE: PRT
<213> ORGANISM: Homo sapiens

<400> SEQUENCE: 4

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg
                20                  25                  30

<210> SEQ ID NO 5
<211> LENGTH: 40
<212> TYPE: PRT
<213> ORGANISM: Artificial Sequence
<220> FEATURE:
<223> OTHER INFORMATION: Synthetic Peptides
<220> FEATURE:
<221> NAME/KEY: Non-natural amino acid
<222> LOCATION: 40
<223> OTHER INFORMATION: (S)-2-amino-4-pentynoic acid

<400> SEQUENCE: 5

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
                20                  25                  30

Ser Gly Ala Pro Pro Ser Xaa
            35          40
```